United States Patent
Wu et al.

(10) Patent No.: US 11,008,338 B2
(45) Date of Patent: May 18, 2021

(54) C5-C6-OXACYCLIC FUSED IMINOTHIAZINE DIOXIDE COMPOUNDS BEARING AN ETHER LINKER AS BACE INHIBITORS, COMPOSITIONS, AND THEIR USE

(71) Applicant: Merck Sharp & Dohme Corp., Rahway, NJ (US)

(72) Inventors: Wen-Lian Wu, Green Brook, NJ (US); Jared N. Cumming, Winchester, MA (US); Brandon M. Taoka, San Francisco, CA (US); Xing Dai, Short Hills, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/821,001

(22) Filed: Mar. 17, 2020

(65) Prior Publication Data

US 2020/0216466 A1   Jul. 9, 2020

Related U.S. Application Data

(63) Continuation of application No. 16/076,813, filed as application No. PCT/US2017/016634 on Feb. 6, 2017, now Pat. No. 10,689,401.

(60) Provisional application No. 62/293,980, filed on Feb. 11, 2016.

(51) Int. Cl.
| | | |
|---|---|---|
| *C07D 513/02* | (2006.01) | |
| *C07D 513/04* | (2006.01) | |
| *C07D 513/10* | (2006.01) | |
| *A61P 25/28* | (2006.01) | |

(52) U.S. Cl.
CPC ............ *C07D 513/02* (2013.01); *A61P 25/28* (2018.01); *C07D 513/04* (2013.01); *C07D 513/10* (2013.01)

(58) Field of Classification Search
CPC ... C07D 513/02; C07D 513/04; C07D 513/10
See application file for complete search history.

(56) References Cited

U.S. PATENT DOCUMENTS

| | | | |
|---|---|---|---|
| 7,763,609 B2 | 7/2010 | Zhu et al. | |
| 7,868,000 B2 | 1/2011 | Zhu et al. | |
| 8,183,252 B2 | 5/2012 | Zhu et al. | |
| 8,691,831 B2 | 4/2014 | Zhu et al. | |
| 8,691,833 B2 | 4/2014 | Zhu et al. | |
| 8,829,036 B2 | 9/2014 | Zhu et al. | |
| 9,096,615 B2 | 8/2015 | Lewis et al. | |
| 9,221,839 B2 | 12/2015 | Cumming et al. | |
| 9,365,589 B2 | 6/2016 | Cumming et al. | |
| 9,556,135 B2 | 1/2017 | Lewis et al. | |
| 9,768,450 B2 | 9/2017 | Song et al. | |
| 10,689,401 B2 * | 6/2020 | Wu ..................... | C07D 513/10 |
| 2014/0023668 A1 | 1/2014 | Cumming et al. | |
| 2015/0344500 A1 | 12/2015 | Cumming et al. | |
| 2017/0362248 A1 | 12/2017 | Dai et al. | |

FOREIGN PATENT DOCUMENTS

| | | |
|---|---|---|
| WO | 2014059185 A1 | 4/2014 |
| WO | 2014099794 A1 | 6/2014 |

OTHER PUBLICATIONS

International Search Report for PCT/US2017/016634 dated May 1, 2017, 8 pages.

\* cited by examiner

*Primary Examiner* — Rebecca L Anderson
(74) *Attorney, Agent, or Firm* — Jeffrey P. Bergman; Catherine D. Fitch

(57) ABSTRACT

In its many embodiments, the present invention provides certain C5-C6-oxacyclic fused iminothiazine dioxide compounds bearing an ether linker, including compounds Formula (I):

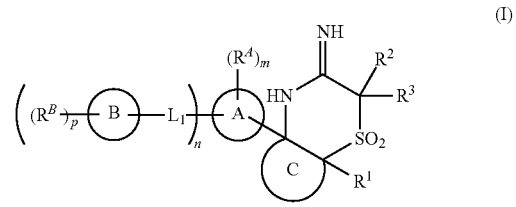

or a tautomer thereof, and pharmaceutically acceptable salts of said compounds and said tautomers, wherein $R^1$, $R^2$, $R^3$, $R^A$, ring A, m, n, -$L_1$-, ring B, $R^B$, and p are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including for the possible treatment of Alzheimer's disease, are also disclosed.

10 Claims, No Drawings

C5-C6-OXACYCLIC FUSED IMINOTHIAZINE DIOXIDE COMPOUNDS BEARING AN ETHER LINKER AS BACE INHIBITORS, COMPOSITIONS, AND THEIR USE

FIELD OF THE INVENTION

This invention provides certain C5-C6-oxacyclic fused iminothiazine dioxide compounds bearing an ether linker, and compositions comprising these compounds, as inhibitors of BACE, which may be useful for treating or preventing pathologies related thereto, including, but not limited to, Alzheimer's disease.

BACKGROUND

Amyloid beta peptide ("A$\beta$") is a primary component of $\beta$ amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration; neurodegeneration, olfactory impairment (including olfactory impairment associated with Alzheimer's disease, Parkinson's disease, and Down's syndrome), $\beta$-amyloid angiopathy (including cerebral amyloid angiopathy), hereditary cerebral hemorrhage, mild cognitive impairment ("MCI"), glaucoma, amyloidosis, type II diabetes, hemodialysis ($\beta$2 microglobulins and complications arising therefrom), neurodegenerative diseases such as scrapie, bovine spongiform encephalitis, Creutzfeld-Jakob disease, traumatic brain injury and the like.

A$\beta$ peptides are short peptides which are made from the proteolytic break-down of the transmembrane protein called amyloid precursor protein ("APP"). A$\beta$ peptides are made from the cleavage of APP by $\beta$-secretase activity at a position near the N-terminus of A$\beta$, and by gamma-secretase activity at a position near the C-terminus of A$\beta$. (APP is also cleaved by $\alpha$-secretase activity, resulting in the secreted, non-amyloidogenic fragment known as soluble APP$\alpha$.) Beta site APP Cleaving Enzyme ("BACE-1") is regarded as the primary aspartyl protease responsible for the production of A$\beta$ by $\beta$-secretase activity. The inhibition of BACE-1 has been shown to inhibit the production of A$\beta$.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, A$\beta$ peptides, formed through $\beta$-secretase and gamma-secretase activity, can form tertiary structures that aggregate to form amyloid fibrils. A$\beta$ peptides have also been shown to form A$\beta$ oligomers (sometimes referred to as "A$\beta$ aggregates" or "Abeta oligomers"). A$\beta$ oligomers are small multimeric structures composed of 2 to 12 A$\beta$ peptides that are structurally distinct from A$\beta$ fibrils. Amyloid fibrils can deposit outside neurons in dense formations known as senile plaques, neuritic plaques, or diffuse plaques in regions of the brain important to memory and cognition. A$\beta$ oligomers are cytotoxic when injected in the brains of rats or in cell culture. This A$\beta$ plaque formation and deposition and/or A$\beta$ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that A$\beta$, A$\beta$ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of A$\beta$ is regarded as causative. A$\beta$ has been shown to be neurotoxic in culture and in vivo. For example, when injected into the brains of aged primates, fibrillar A$\beta$ causes neuronal cell death around the injection site. Other direct and circumstantial evidence of the role of A$\beta$ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of A$\beta$ levels lead to a dramatic inhibition of A$\beta$-driven AD-like pathology, making $\beta$-secretase a target for therapeutic intervention in AD. Ohno et al. Neurobiology of Disease, No. 26 (2007), 134-145, report that genetic deletion of BACE-1 in 5XFAD mice abrogates A$\beta$ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that A$\beta$ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of $\beta$-secretase activity produces no profound phenotypic defects while inducing a concomitant reduction in A$\beta$. Luo et al., Nature Neuroscience. Vol. 4, No. 3, March 2001, report that mice deficient in BACE-1 have normal phenotype and abolished $\beta$-amyloid generation.

More recently, Jonsson, et al. have reported in Nature. Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002: 855:723-31; Crino P B, Martin J A, Hill W D, et al., Ann Otol Rhinol Laryngol, 1995; 104:655-61: Davies D C, et al., Neurobiol Aging, 1993:14:353-7; Devanand D P, et al., Am J Psychiatr. 2000:157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"). Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example. Kong et al., US2008/0015180, disclose methods and compositions for treating amyloidosis with agents that inhibit Aβ peptide formation. As another example, certain groups have suggested the potential of BACE inhibition may be useful for traumatic brain injury. (Loane et al., "Amyloid precursor protein secretases as therapeutic targets for traumatic brain injury", Nature Medicine, 15, 377-379 (2009): Yu, et al., "Lithium reduces BACE1 overexpression, β amyloid accumulation, and spatial learning deficits in mice with traumatic brain injury", J Neurotrauma, 2012 September; 29(13): 2342-51; Tran, et al., "Controlled cortical impact traumatic brain injury in 3xTg-A D mice causes acute intra-axonal amyloid-β accumulation and independently accelerates the development of tau abnormalities", J Neurosci. 2011 Jun. 29; 31(26):9513-25). Still other diverse pathologies characterized by the inappropriate formation and deposition of Aβ or fragments thereof, and/or by the presence of amyloid fibrils, and/or for which inhibitor(s) of BACE are expected to be of therapeutic value are discussed further hereinbelow.

WO2014/099974 discloses certain fused iminothiazine dioxide compounds having an amide linker as BACE inhibitors. WO2014059185 discloses certain amino-dihydrothiazine and amino-dioxido dihydrothiazine compounds as beta-secretase antagonists. However, there remains a need in the art for novel potent and selective BACE inhibitors. The present invention addresses this need.

SUMMARY OF THE INVENTION

The present invention provides certain C5-C6-oxacyclic fused iminothiazine dioxide compounds bearing an ether linker, which are collectively or individually referred to herein as "compound(s) of the invention", as described herein. The compounds of the invention are inhibitors of BACE-1 and/or BACE-2, and may be useful for treating or preventing diseases or pathologies related thereto.

In one embodiment, the compounds of the invention have the structural Formula (I):

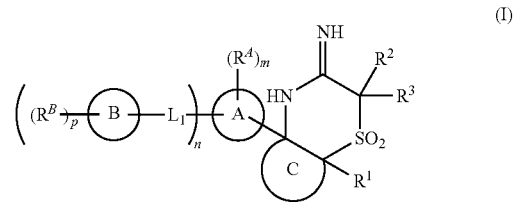

or a tautomer thereof having the structural Formula (I'):

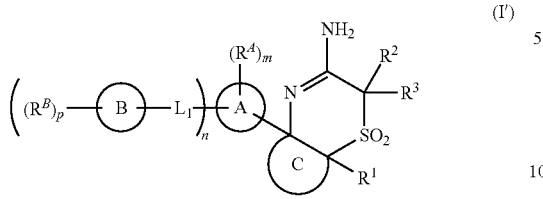

or pharmaceutically acceptable salt thereof, wherein:
ring C is selected from the group consisting of tetrahydrofuranyl and tetrahydropyranyl, wherein 1 or 2 of the ring carbon atoms having two available substitutable hydrogen atoms of said tetrahydrofuranyl and tetrahydropyranyl rings are optionally independently replaced with a —C($R^{C1}R^{C2}$)— group,
  wherein $R^{C1}$ and $R^{C2}$ are each independently selected from the group consisting of H, halogen, —$CO_2$—($C_1$-$C_6$-alkyl), alkyl, cycloalkyl, -alkyl-cycloalkyl, heterocycloalkyl, -alkyl-heterocycloalkyl, aryl, -alkyl-aryl, heteroaryl, and alkyl-heteroaryl,
    wherein each said alkyl, cycloalkyl, heterocycloalkyl, aryl, and heteroaryl of $R^{C1}$ and $R^{C2}$ are optionally substituted with one or more $R^3$, and
    wherein 1 to 2 non-adjacent, non-terminal carbon atoms in each said alkyl of $R^{C1}$ and $R^{C2}$ are optionally independently replaced with —O—, —NH—, —N($C_1$-$C_6$-alkyl)-, —S—, —S(O)—, or —S(O)$_2$—,
or, alternatively, wherein said $R^{C1}$ and $R^{C2}$ of one said —C($R^{C1}R^{C2}$)— group are taken together with the carbon to which they are attached form a spirocyclic ring consisting of from 3 to 6 carbon atoms,
  wherein 1 of said carbon atoms may be replaced with —O—, —NH—, —N($C_1$-$C_6$-alkyl)-, —N($C_1$-$C_6$-haloalkyl)-, —S—, —S(O)—, or —S(O)$_2$—, and
  wherein 1 to 2 of the carbon atoms of said spirocyclic ring may be optionally independently substituted with 1 to 2 fluorine, $C_1$-$C_6$-alkyl, $C_1$-$C_6$-haloalkyl, or —$CH_2$O—($C_1$-$C_6$-alkyl):
$R^1$ is selected from the group consisting of H, halogen, and alkyl, wherein said alkyl is optionally substituted with one or more fluorine, and
  wherein 1 to 2 non-adjacent, non-terminal carbon atoms in said alkyl are optionally independently replaced with —O—, —NH—, —N(alkyl)-, —S—, —S(O)—, or —S(O)$_2$—;
$R^2$ and $R^3$ are each independently selected from the group consisting of H, halogen, alkyl, cycloalkyl, -alkyl-cycloalkyl, heterocycloalkyl, -alkyl-heterocycloalkyl, aryl, -alkyl-aryl, heteroaryl, and alkyl-heteroaryl,
  wherein each said alkyl, cycloalkyl, heterocycloalkyl, aryl, and heteroaryl of $R^2$ and $R^3$ are optionally substituted with one or more $R^4$, and
  wherein 1 to 2 non-adjacent, non-terminal carbon atoms in each said alkyl of $R^2$ and $R^3$ are optionally independently replaced with —O—, —NH—, —N($C_1$-$C_3$-alkyl)-, —S—, —S(O)—, or —S(O)$_2$—,
or, alternatively, $R^2$ and $R^3$ are taken together with the carbon to which they are attached form a spirocyclic ring consisting of from 3 to 6 carbon atoms.
  wherein 1 of said carbon atoms may be replaced with —O—, —NH—, —N($C_1$-$C_3$-alkyl)-, —N($C_1$-$C_3$-haloalkyl)-, —S—, —S(O)—, or —S(O)$_2$—, and
  wherein 1 to 2 of the carbon atoms of said spirocyclic ring may be optionally independently substituted with 1 to 2 fluorine, $C_1$-$C_3$-alkyl, $C_1$-$C_3$-haloalkyl, or —$CH_2$O—($C_1$-$C_3$-alkyl):
ring A is selected from the group consisting of aryl and heteroaryl:
m is 0 or more, with the proviso that the value of m does not exceed the number of available substitutable hydrogen atoms on ring A;
each $R^A$ (when present) is independently selected from the group consisting of halogen, oxo, —OH, —CN, alkyl, —O-alkyl, and cycloalkyl,
  wherein said alkyl, —O-alkyl, and cycloalkyl of $R^A$ are each optionally independently unsubstituted or substituted with one or more fluorine, and
  wherein 1 to 2 non-adjacent, non-terminal carbon atoms in said alkyl and —O-alkyl are optionally independently replaced with —O—, —NH—, —N($C_1$-$C_3$-alkyl)-, —S—, —S(O)—, or —S(O)$_2$—,
n is 0 or 1;
-$L_1$- (when present) independently represents a bond or a divalent moiety selected from the group consisting of —O—, —$CH_2$O—, —CH($CH_3$)O—, —CH($CF_3$)O—, and —CH($CHF_2$)O—:
ring B is selected from the group consisting of aryl, heteroaryl, cycloalkyl, and heterocycloalkyl;
p is 0 or more, with the proviso that the value of p does not exceed the number of available substitutable hydrogen atoms on ring B; and
each $R^B$ (when present) is independently selected from the group consisting of halogen, oxo, —OH, —CN, —$SF_5$, —$OSF_5$, —$OR^{B1}$, —$SR^{B1}$, alkyl, alkenyl, alkynyl, cycloalkyl, -alkyl-cycloalkyl, heterocycloalkyl, -alkyl-heterocycloalkyl, aryl, and heteroaryl,
  wherein said each alkyl, alkenyl, alkynyl, cycloalkyl, heterocycloalkyl, aryl, and heteroaryl of $R^B$ are each optionally independently unsubstituted or substituted with one or more groups independently selected from $R^4$, and wherein 1 to 2 non-adjacent, non-terminal carbon atoms in said alkyl are optionally independently replaced with —O—, —NH—, —N(alkyl)-, —S—, —S(O)—, or —S(O)$_2$—;
each $R^{B1}$ is independently selected from the group consisting of H, alkyl, alkenyl, alkynyl, cycloalkyl, -alkyl-cycloalkyl, heterocycloalkyl, and alkyl-heterocycloalkyl,
  wherein each said alkyl, alkenyl, alkynyl, cycloalkyl, and heterocycloalkyl, of $R^{B1}$ is unsubstituted or optionally substituted with one or more fluorine, and
  wherein 1 to 2 non-adjacent, non-terminal carbon atoms in said alkyl are optionally independently replaced with —O—, —NH—, —N($C_1$-$C_6$-alkyl)-, —S—, —S(O)—, or —S(O)$_2$—;
each $R^4$ (when present) is independently selected from the group consisting of halogen, —OH, —CN, $C_1$-$C_6$-alkyl, —($C_1$-$C_6$-alkyl)-OH, —O—($C_1$-$C_6$-alkyl), cycloalkyl, —($C_1$-$C_6$-alkyl)-cycloalkyl, —O-cycloalkyl, —O—($C_1$-$C_6$-alkyl)-cycloalkyl, heterocycloalkyl, —($C_1$-$C_6$-alkyl)-heterocycloalkyl, —O-heterocycloalkyl and —O—($C_1$-$C_6$-alkyl)-heterocycloalkyl.
  wherein each said $C_1$-$C_6$-alkyl, cycloalkyl, and heterocycloalkyl are optionally substituted with one or more halogen,
  and wherein 1 to 2 non-adjacent, non-terminal carbon atoms in each said $C_1$-$C_6$-alkyl is optionally independently replaced with —O—, —NH—, —N($C_1$-$C_3$-alkyl)-, —S—, —S(O)—, or —S(O)$_2$—.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I), (I'), (IA), or (IA'). In each of the embodiments described herein, each variable is selected independently of the other unless otherwise noted.

In one embodiment, the compounds of the invention have the structural Formula (IA):

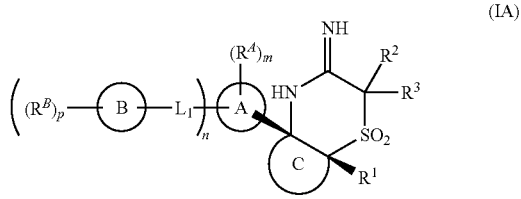

or a tautomer thereof having the structural Formula (IA'):

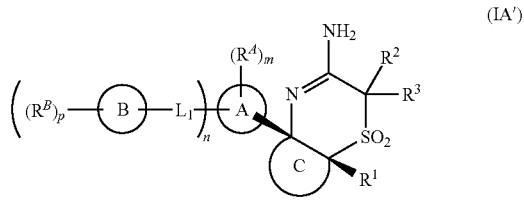

or pharmaceutically acceptable salt thereof, wherein each variable is as described in Formula (I).

In one embodiment, in each of Formulas (I), (I'), (IA), and (IA'):
ring C is selected from the group consisting of

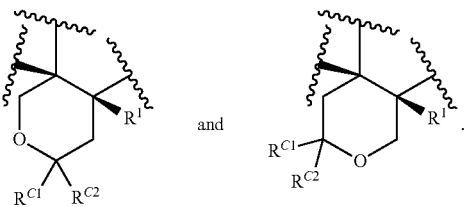

In one embodiment, in each of Formulas (I), (I'), (IA), and (IA'):
ring C is

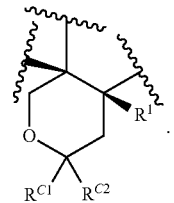

The following alternative embodiments of $R^{C1}$ and $R^{C2}$ are contemplated in combination with any of the embodiments described above.

In one embodiment, in each of Formulas (I), (I'), (IA), and (IA'):
$R^{C1}$ and $R^{C2}$ are each independently selected from the group consisting of H, —CO$_2$CH$_3$, —CO$_2$CH$_2$CH$_3$, —CO$_2$CH(CH$_3$)$_3$, methyl, ethyl, propyl, butyl, cyclopropyl, —CH$_2$-cyclopropyl, cyclobutyl, —CH$_2$-cyclobutyl, —CH$_2$OH, —CH$_2$OCH$_3$, —CH$_2$OCH$_2$CH$_3$, phenyl, pyridyl, pyrimidinyl, pyrazinyl, oxazoyl, isooxazoyl, thiazoyl, isothiazolyl, pyrazolyl, benzodioxolyl, benzofuranyl, dihydrobenzofuranyl, benzyl, —CH$_2$-pyridyl, —CH$_2$-pyrimidinyl, and —CH$_2$-pyrazinyl,
wherein each said methyl, ethyl, propyl, butyl, cyclopropyl, —CH$_2$-cyclopropyl, cyclobutyl, —CH$_2$-cyclobutyl, —CH$_2$OCH$_3$, and —CH$_2$OCH$_2$CH$_3$ of $R^{C1}$ and $R^{C2}$ is optionally substituted with one or more fluorine, and
wherein each said phenyl, pyridyl, pyrimidinyl, pyrazinyl, oxazoyl, isoxazoyl, thiazoyl, isothiazolyl, pyrazolyl, benzodioxolyl, benzofuranyl, dihydrobenzofuranyl, benzyl, —CH$_2$-pyridyl, —CH$_2$-pyrimidinyl, and —CH$_2$-pyrazinyl of $R^{C1}$ and $R^{C2}$ is unsubstituted or substituted with one or more groups independently selected from the group consisting of fluorine, chlorine, bromine, methyl, ethyl, propyl, cyclopropyl, —OCH$_3$, —OCH$_2$CH$_3$, and —O-cyclopropyl,
wherein each said methyl, ethyl, propyl, cyclopropyl, —OCH$_3$, —OCH$_2$CH$_3$, and —O-cyclopropyl is each optionally substituted with from 1 to 3 fluorine.

In one embodiment, in each of Formulas (I), (I'), (IA), and (IA'):
$R^{C1}$ and $R^{C2}$ are each independently selected from the group consisting of H, —CO$_2$CH$_3$, methyl, ethyl, propyl, cyclopropyl, —CH$_2$OH, —CH$_2$OCH$_3$, phenyl, pyridyl, pyrimidinyl, oxazoyl, isoxazoyl, and pyrazolyl,
wherein each said methyl, ethyl, propyl, cyclopropyl, and —CH$_2$OCH$_3$, of $R^{C1}$ and $R^{C2}$ is optionally substituted with one or more fluorine, and
wherein each said phenyl, pyridyl, pyrimidinyl, oxazoyl, isoxazoyl, and pyrazolyl of $R^{C1}$ and $R^{C2}$ is unsubstituted or substituted with one or more groups independently selected from the group consisting of fluorine, methyl, ethyl, cyclopropyl, and —OCH$_3$,
   wherein each said methyl, ethyl, cyclopropyl, and —OCH$_3$ is each optionally substituted with from 1 to 3 fluorine.

In one embodiment, in each of Formulas (I), (I'), (IA), and (IA'):
$R^{C1}$ and $R^{C2}$ are each independently selected from the group consisting of H, —CO$_2$CH$_3$, methyl, propyl, —CHF$_2$, cyclopropyl, —CH$_2$OH, —CH$_2$OCH$_3$, phenyl, and isoxazoyl,
   wherein each said phenyl and isoxazoyl of $R^{C1}$ and $R^{C2}$ is unsubstituted or substituted with one or more groups independently selected from the group consisting of fluorine and methyl.

In one embodiment, in each of Formulas (I), (I'), (IA), and (IA'):
$R^{C1}$ and $R^{C2}$ are each independently selected from the group consisting of H, methyl, propyl, —CH$_2$OH, and phenyl,
   wherein each said phenyl of $R^{C1}$ and $R^{C2}$ is unsubstituted or substituted with one or more fluorine.

In one embodiment, in each of Formulas (I), (I'), (IA), and (IA'):
$R^{C2}$ is selected from the group consisting of H and methyl.

In one embodiment, in each of Formulas (I), (I'), (IA), and (IA'): $R^{C1}$ is selected from the group consisting of H, —CO$_2$CH$_3$, methyl, ethyl, propyl, cyclopropyl, —CH$_2$OH, —CH$_2$OCH$_3$, phenyl, pyridyl, pyrimidinyl, oxazoyl, isoxazoyl, and pyrazolyl,
   wherein each said methyl, ethyl, propyl, cyclopropyl, and —CH$_2$OCH$_3$, of $R^{C1}$ is optionally substituted with one or more fluorine, and
   wherein each said phenyl, pyridyl, pyrimidinyl, oxazoyl, isoxazoyl, and pyrazolyl of $R^{C1}$ is unsubstituted or substituted with one or more groups independently selected from the group consisting of fluorine, methyl, ethyl, cyclopropyl, and —OCH$_3$,
      wherein each said methyl, ethyl, cyclopropyl, and —OCH$_3$ is each optionally substituted with from 1 to 3 fluorine; and
$R^{C2}$ is selected from the group consisting of H and methyl.

In one embodiment, in each of Formulas (I), (I'), (IA), and (IA'):
$R^{C1}$ is selected from the group consisting of H, —CO$_2$CH$_3$, methyl, propyl, —CHF$_2$, cyclopropyl, —CH$_2$OH, —CH$_2$OCH$_3$, phenyl, and isoxazoyl,
   wherein each said phenyl and isoxazoyl of $R^{C1}$ is unsubstituted or substituted with one or more groups independently selected from the group consisting of fluorine and methyl; and
$R^{C2}$ is selected from the group consisting of H and methyl.

In one embodiment, in each of Formulas (I), (I'), (IA), and (IA'):
$R^{C1}$ is selected from the group consisting of H, methyl, propyl, —CH$_2$OH, and phenyl,
   wherein said phenyl of $R^{C1}$ is unsubstituted or substituted with one or more fluorine; and
$R^{C2}$ is selected from the group consisting of H and methyl.

In one embodiment, in each of Formulas (I), (I'), (IA), and (IA'):
ring C is

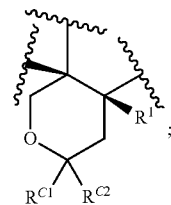

and
$R^{C1}$ and $R^C$ are each independently selected from the group consisting of H, —CO$_2$CH$_3$, methyl, propyl, —CHF$_2$, cyclopropyl, —CH$_2$OH, —CH$_2$CH$_3$, phenyl, and isoxazoyl,
   wherein each said phenyl and isoxazoyl of $R^{C1}$ and $R^{C2}$ is unsubstituted or substituted with one or more groups independently selected from the group consisting of fluorine and methyl.

In one embodiment, in each of Formulas (I), (I'), (IA), and (IA'):
ring C is

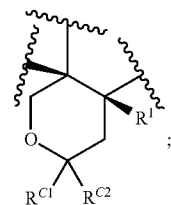

$R^{C1}$ is selected from the group consisting of H, methyl, propyl, —CH$_2$OH, and phenyl.
   wherein said phenyl of $R^{C1}$ is unsubstituted or substituted with one or more fluorine; and
$R^{C2}$ is selected from the group consisting of H and methyl.

In one embodiment, in each of Formulas (I), (I'), (IA), and (IA'):
ring C is

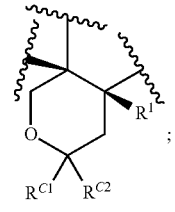

and
$R^{C1}$ and $R^{C2}$ taken together with the carbon to which they are attached form a spirocyclic ring selected from the group consisting of spirocyclopropyl, spirocyclobutyl, spirocyclopentyl, spirocyclohexyl, spiroazetidinyl, spiropyrrolidinyl, spiropiperidinyl, spiroxetanyl, spirotetrahydrofuranyl, spirotetrahydropyranyl,
   wherein each of the carbon atoms of said spirocyclopropyl, spirocyclobutyl, spirocyclopentyl, spirocyclohexyl, spiroazetidinyl, spiropyrrolidinyl, spiropiperidinyl, spiroxetanyl, spirotetrahydrofuranyl, spirotetrahydropyranyl is unsubstituted or substituted with 1 to 4 groups independently selected from the group consisting of fluorine, methyl, cyclopropyl, and —OCH$_3$, wherein each said methyl, cyclopropyl, and —OCH$_3$ is each optionally substituted with from 1 to 3 fluorine,
and wherein each of the nitrogen atoms of said spiroazetidinyl, spiropyrrolidinyl, and spiropiperidinyl is unsubstituted or substituted with methyl, ethyl, propyl, and —CH$_2$CF$_3$.

The following alternative embodiments of R$^1$ are contemplated in combination with any of the embodiments described above.

In one embodiment, in each of Formulas (I), (I'), (IA), and (IA'):
R$^1$ is selected from the group consisting of H, fluoro, methyl, and —CH$_2$OCH$_3$.

In one embodiment, in each of Formulas (I), (I'), (IA), and (IA'):
R$^1$ is H.

The following alternative embodiments of R$^2$ and R$^3$ are contemplated in combination with any of the embodiments described above.

In one embodiment, in each of Formulas (I), (I'), (IA), and (IA'):
R$^2$ and R$^3$ are each independently selected from the group consisting of H, fluoro, methyl, ethyl, propyl, butyl, —CF$_3$, —CHF$_2$, —CH$_2$F, —CH$_2$CF$_3$, —CF$_2$CH$_3$, —CH$_2$OCH$_3$, —CH$_2$OCH$_2$CH$_3$, —CH$_2$CH$_2$OCH$_3$, —CH$_2$SCH$_3$, —CH$_2$SCH$_2$CH$_3$, —CH$_2$CH$_2$SCH$_3$, —CH$_2$N(CH$_3$)$_2$, —CH$_2$NHCH$_3$, —CH$_2$CH$_2$N(CH$_3$)$_2$, —CH$_2$OCF$_3$, —CH$_2$OCHF$_2$, azetidinyl, cyclobutyl, —CH$_2$-cyclopropyl, imidazolyl, isothiazolyl, isoxazolyl, oxadiazolyl, oxazolyl, oxetanyl, phenyl, —CH$_2$-phenyl, piperazinyl, pyrazinyl, pyrazolyl, pyridazinyl, pyridyl, pyrimidinyl, tetrahydrofuranyl, tetrahydropyranyl, thiadiazolyl, thiazolyl, and thienyl,
wherein each said azetidinyl, cyclobutyl, —CH$_2$-cyclopropyl, imidazolyl, isothiazolyl, isoxazolyl, oxadiazolyl, oxazolyl, oxetanyl, phenyl, —CH$_2$-phenyl, piperazinyl, pyrazinyl, pyrazolyl, pyridazinyl, pyridyl, pyrimidinyl, tetrahydrofuranyl, tetrahydropyranyl, thiadiazolyl, thiazolyl, and thienyl of R$^2$ and R$^3$ are is unsubstituted or substituted with one or more groups independently selected from the group consisting of fluorine, methyl, ethyl, cyclopropyl, and —OCH$_3$.
wherein each said methyl, ethyl, cyclopropyl, and —OCH$_3$ is each optionally substituted with from 1 to 3 fluorine;

In one embodiment, in each of Formulas (I), (I'), (IA), and (IA'):
R$^2$ and R$^3$ are each independently selected from the group consisting of H, fluoro, methyl, —CF$_3$, —CHF$_2$, —CH$_2$F, —CH$_2$OCH$_3$, —CH$_2$N(CH$_3$)$_2$, azetidinyl, cyclopropyl, cyclobutyl, oxetanyl, phenyl, pyrazinyl, pyridyl, pyrimidinyl, tetrahydrofuranyl, and tetrahydropyranyl.
wherein each said azetidinyl, cyclopropyl, cyclobutyl, oxetanyl, phenyl, pyrazinyl, pyridyl, pyrimidinyl, tetrahydrofuranyl, and tetrahydropyranyl or R$^2$ and R$^3$ are unsubstituted or substituted with one or two groups independently selected from the group consisting of fluorine, methyl, ethyl, cyclopropyl, and —OCH$_3$,
wherein each said methyl, ethyl, cyclopropyl, and —OCH$_3$ is each optionally substituted with from 1 to 3 fluorine.

In one embodiment, in each of Formulas (I), (I'), (IA), and (IA'):
R$^2$ and R$^3$ are each independently selected from the group consisting of methyl, —CHF$_2$, and —CH$_2$F, cyclopropyl, phenyl, pyridyl, and tetrahydropyranyl.
wherein each said cyclopropyl, phenyl, pyridyl, tetrahydropyranyl of R$^2$ and R$^3$ are unsubstituted or substituted with one or two groups independently selected from the group consisting of fluorine, methyl, ethyl, cyclopropyl, and —OCH$_3$,
wherein each said methyl, ethyl, cyclopropyl, and —OCH$_3$ is each optionally substituted with from 1 to 3 fluorine.

In one embodiment, in each of Formulas (I), (I'), (IA), and (IA'):
R$^2$ and R$^3$ are methyl.

In some embodiments, in each of Formulas (I), (I'), (IA), and (IA'):
n is 1. In these embodiments, the moiety:

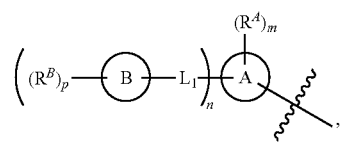

has the form:

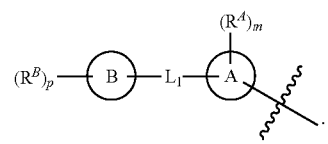

The following alternative embodiments of n and -L$_1$- are contemplated in combination with any of the embodiments described above.

In one embodiment, in each of Formulas (I), (I'), (IA), and (IA'):
n is 1; and
-L$_1$- independently represents a bond or a divalent moiety selected from the group consisting of —O— and —CH$_2$O—.

In one embodiment, in each of Formulas (I), (I'), (IA), and (IA'):
n is 1; and
-L$_1$- is a bond.

In one embodiment, in each of Formulas (I), (I'), (IA), and (IA'):
n is 1; and
-L$_1$- is —O—.

In one embodiment, in each of Formulas (I), (I'), (IA), and (IA'):
n is 1; and
-L$_1$- is —CH$_2$O—.

The following alternative embodiments of ring A, R$^A$, m, n, ring B, p, and R$^B$ are contemplated in combination with any of the embodiments described above.

In one embodiment, in each of Formulas (I), (I'), (IA), and (IA'):
n is 1;
ring A is selected from the group consisting of phenyl, pyridazinyl, pyridinyl, pyrimidinyl, pyrazinyl, pyrazolyl, triazinyl, thiazolyl, and thienyl;
m is 0, 1, 2, or 3; with the proviso that the value of m does not exceed the number of available substitutable hydrogen atoms on ring A; and
each R$^A$ (when present) is independently selected from the group consisting of fluoro, chloro, bromo, —CN, methyl, ethyl, cyclopropyl, —CH$_2$OCH$_3$, —CF$_3$, —CHF$_2$, —CH$_2$F, —OCH$_3$, —OCF$_3$, and —OCHF$_2$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3 with the proviso that the value of m does not exceed the number of available substitutable hydrogen atoms on ring A.

In one embodiment, in each of Formulas (I), (I'), (IA), and (IA'):

n is 1:

ring A is selected from the group consisting of phenyl, pyridinyl, and thienyl;

m is 0, 1, 2, or 3; with the proviso that the value of m does not exceed the number of available substitutable hydrogen atoms on ring A; and each R$^A$ (when present) is independently selected from the group consisting of fluoro, chloro, methyl, and —CHF$_2$.

In an alternative of the immediately embodiment, m is 0. In another alternative of the immediately preceding embodiment, m is 1. In another alternative of the immediately preceding embodiment, m is 2. In another alternative of the immediately preceding embodiment, m is 3, with the proviso that the value of m does not exceed the number of available substitutable hydrogen atoms on ring A.

In one embodiment, in each of Formulas (I), (I'), (IA), and (IA'):

n is 1:

ring A is selected from the group consisting of phenyl and pyridinyl:

m is 0, 1, 2, or 3; and each R$^A$ (when present) is independently selected from the group consisting of fluoro, chloro, methyl, and —CHF$_2$.

In an alternative of the immediately embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), and (IA'):

n is 1;

ring A is selected from the group consisting of phenyl and pyridinyl:

m is 0, 1, 2, or 3; and each R$^A$ (when present) is fluoro.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (1'), (IA), and (IA'):

n is 1:

ring A is phenyl;

m is 0, 1, or 2; and each R$^A$ (when present) is fluoro.

In an alternative of the immediately preceding embodiment, m is 0. In another alternative of the immediately preceding embodiment, m is 1. In another alternative of the immediately preceding embodiment, m is 2.

In one embodiment, in each of Formulas (I), (I'), (IA), and (IA'):

n=1;

-L$_1$- is —O—;

ring B is selected from the group consisting of azetidinyl, benzimidazolyl, benzoisothiazolyl benzoisoxazolyl, benzothiazolyl, benzoxazolyl, cyclobutyl, cyclohexyl, cyclopentyl, cyclopropyl, dihydroindenyl, furanyl, imidazolyl, imidazopyridinyl, imidazopyrimidinyl, imidazothiazolyl, indenyl, indolyl, isothiazolyl, isoxazolyl, morpholinyl, oxadiazolyl, oxazolyl, oxetanyl, phenyl, piperazinyl, piperidinyl, pyrazinyl, pyrazolyl, pyrazolopyridinyl, pyrazolopyrimidinyl, pyridazinyl, pyridinyl, pyrimidinyl, pyrazolopyridinyl, pyrrolidinyl, pyrrolyl, pyrazolopyridinyl, pyrrolopyrimidinyl, tetrahydrofuranyl, tetrahydropyranyl, tetrazolyl, thiadiazolyl, thiazolyl, thienyl, thienylpyridine, thiomorpholinyl, thiomorpholinyl dioxide, and triazolyl;

p is 0, 1, 2, or 3, with the proviso that the value of p does not exceed the number of available substitutable hydrogen atoms on ring B; and each R$^B$ group (when present) is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridinyl, oxadiazolyl, isoxazolyl, oxazolyl, pyrazolyl, pyrrolyl, and triazolyl, wherein each said phenyl, pyridinyl, oxadiazolyl, isoxazolyl, oxazolyl, pyrazolyl, pyrrolyl, and triazolyl is optionally substituted with from 1 to 3 substituents independently selected from the group consisting of fluoro, chloro, —CN, methyl, —OCH$_3$, and —CF$_3$;

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):

n=1;

-L$_1$- is —O—;

ring B is selected from the group consisting of cyclobutyl, cyclopentyl, cyclopropyl, phenyl, piperidinyl, pyrazinyl, pyrazolyl, pyridazinyl, pyridinyl, pyrimidinyl, pyrrolidinyl, tetrahydrofuranyl, tetrahydropyranyl;

p is 0, 1, 2, or 3, with the proviso that the value of p does not exceed the number of available substitutable hydrogen atoms on ring B; and each R$^B$ group (when present) is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡C—CH$_3$, —CF$_3$, —CHF$_2$, —OCF$_3$, —OCHF$_2$, oxadiazolyl, isoxazolyl, oxazolyl, pyrazolyl, pyrrolyl, and triazolyl, wherein each said oxadiazolyl, isoxazolyl, oxazolyl, pyrazolyl, pyrrolyl, and triazolyl, is optionally substituted with one substituent from the group consisting of fluoro and methyl.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):
n=1;
-L$_1$- is —O—:
ring B is selected from the group consisting of cyclobutyl, phenyl, pyrazinyl, pyridazinyl, pyridinyl, and pyrimidinyl:
p is 0, 1, or 2; and
each R$^B$ group (when present) is independently selected from the group consisting of fluoro, methyl, —CN, —OMe, —CHF$_2$, oxazolyl, pyrazolyl, and triazolyl, wherein each said oxadiazolyl, pyrazolyl, and triazolyl, is optionally substituted with one substituent from the group consisting of fluoro and methyl.

In an alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):
n=1;
-L$_1$- is —O—:
ring B is selected from the group consisting of cyclobutyl, pyrazinyl, pyridinyl, and pyrimidinyl;
p is 0, 1, or 2; and
each R$^B$ group (when present) is independently selected from the group consisting of fluoro, methyl, —CN, —OMe, and —CHF$_2$.

In an alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):
n=1;
-L$_1$- is —O—:
ring B is selected from the group consisting of cyclobutyl and pyridinyl:
p is 0, 1, or 2; and
each R$^B$ group (when present) is independently selected from the group consisting of fluoro and —CN.

In an alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):
n=1;
-L$_1$- is —O—;
ring A is selected from the group consisting of phenyl and pyridinyl;
m is 0, 1, 2, or 3;
each R$^A$ (when present) is fluoro;
ring B is selected from the group consisting of cyclobutyl, cyclopentyl, cyclopropyl, phenyl, piperidinyl, pyrazinyl, pyrazolyl, pyridazinyl, pyridinyl, pyrimidinyl, pyrrolidinyl, tetrahydrofuranyl, tetrahydropyranyl;
p is 0, 1, 2, or 3, with the proviso that the value of p does not exceed the number of available substitutable hydrogen atoms on ring B; and
each R$^B$ group (when present) is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡C—CH$_3$, —CF$_3$, —CHF$_2$, —OCF$_3$, —OCHF$_2$, oxadiazolyl, isoxazolyl, oxazolyl, pyrazolyl, pyrrolyl, and triazolyl,
wherein each said oxadiazolyl, isoxazolyl, oxazolyl, pyrazolyl, pyrrolyl, and triazolyl, is optionally substituted with one substituent from the group consisting of fluoro and methyl.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In another alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):
n=1;
-L$_1$- is —O—:
ring A is selected from the group consisting of phenyl and pyridinyl;
m is 0, 1, 2, or 3;
each R$^A$ (when present) is fluoro:
ring B is selected from the group consisting of cyclobutyl, pyrazinyl, pyridinyl, and pyrimidinyl:
p is 0, 1, or 2; and
each R$^B$ group (when present) is independently selected from the group consisting of fluoro, methyl, —CN, —OMe, and —CHF$_2$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In another alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):
n=1;
-L$_1$- is —O—;
ring A is selected from the group consisting of phenyl and pyridinyl;
m is 0, 1, or 2;
each R$^A$ (when present) is fluoro;
ring B is selected from the group consisting of cyclobutyl and pyridinyl;
p is 0, 1, or 2; and
each R$^B$ group (when present) is independently selected from the group consisting of fluoro and —CN.

In an alternative of the immediately preceding embodiment, m is 0. In another alternative of the immediately preceding embodiment, m is 1. In another alternative of the immediately preceding embodiment, m is 2.

In another alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):
n=1;
-L$_1$- is —O—;
ring A is phenyl;

m is 0, 1, or 2;

each $R^A$ (when present) is fluoro:

ring B is selected from the group consisting of cyclobutyl and pyridinyl;

p is 0, 1, or 2; and each $R^B$ group (when present) is independently selected from the group consisting of fluoro and —CN.

In an alternative of the immediately preceding embodiment, m is 0. In another alternative of the immediately preceding embodiment, m is 1. In another alternative of the immediately preceding embodiment, m is 2.

In another alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):

n=1;

-$L_1$- is —CH$_2$O—;

ring B is selected from the group consisting of azetidinyl, bicyclo[2.1.1]hexane, bicyclo[3.1.1]heptane, bicyclo[2.2.1]heptane, bicyclo[2.2.2]octane, [1.1.1]-bicyclopentane, cyclobutyl, cyclohexyl, cyclopentyl, cyclopropyl, furanyl, isothiazolyl, isoxazolyl, morpholinyl, oxadiazolyl, oxazolyl, oxetanyl, phenyl, piperazinyl, piperidinyl, pyrazinyl, pyrazolyl, pyridazinyl, pyridinyl, pyrimidinyl, pyrrolidinyl, pyrrolyl, tetrahydrofuranyl, tetrahydropyranyl, tetrazolyl, thiadiazolyl, thiazolyl, thienyl, thiomorpholinyl, thiomorpholinyl dioxide, and triazolyl:

p is 0, 1, 2, or 3, with the proviso that the value of p does not exceed the number of available substitutable hydrogen atoms on ring B; and each $R^B$ group (when present) is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, and —OCH$_2$CH$_2$F.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):

n=1;

-$L_1$- is —CH$_2$O—;

ring B is selected from the group consisting of [1.1.1]-bicyclopentane, cyclobutyl, cyclopropyl, oxazolyl, phenyl, pyrazinyl, pyridinyl, pyrimidinyl, tetrahydropyranyl, and thiazolyl;

p is 0, 1, 2, or 3, with the proviso that the value of p does not exceed the number of available substitutable hydrogen atoms on ring B; and each $R^B$ group (when present) is independently selected from the group consisting of fluoro, chloro, —CN, —OCH$_3$, —OCH$_2$—C≡C—H, —OCH$_2$—C≡C—CH$_3$, methyl, cyclopropyl, —CH$_2$OCH$_3$, —C≡CH, —C≡C—CH$_3$, —CF$_3$, —CHF$_2$, —OCF$_3$, and —OCHF$_2$.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I), (IA), and (IA'):

n=1;

-$L_1$- is —CH$_2$O—;

ring B is selected from the group consisting of [1.1.1]-bicyclopentane, cyclobutyl, and cyclopropyl;

p is 0, 1, or 2; and each $R^B$ group (when present) is independently selected from the group consisting of fluoro, —CN, and —OMe.

In an alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):

n=1;

-$L_1$- is —CH$_2$O—; and ring B is cyclopropyl;

In one embodiment, in each of Formulas (I), (I), (IA), and (IA'):

n is 1;

-$L_1$- is —CH$_2$O—;

ring A is selected from the group consisting of phenyl and pyridinyl;

m is 0, 1, 2, or 3;

each $R^A$ (when present) is fluoro;

ring B is selected from the group consisting of [1.1.1]-bicyclopentane, cyclobutyl, cyclopropyl, oxazolyl, phenyl, pyrazinyl, pyridinyl, pyrimidinyl, tetrahydropyranyl, and thiazolyl;

p is 0, 1, 2, or 3, with the proviso that the value of p does not exceed the number of available substitutable hydrogen atoms on ring B; and each $R^B$ group (when present) is independently selected from the group consisting of fluoro, chloro, —CN, —OCH$_3$, —OCH$_2$—C≡C—H, —OCH$_2$—C≡C—CH$_3$, methyl, cyclopropyl, —CH$_2$OCH$_3$, —C≡CH, —C≡C—CH$_3$, —CF$_3$, —CHF$_2$, —OCF$_3$, and —OCHF$_2$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In another alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):

n=1;

-$L_1$- is —CH$_2$O—;

ring A is selected from the group consisting of phenyl and pyridinyl;

m is 0, 1, 2, or 3;

each $R^A$ (when present) is fluoro;

ring B is selected from the group consisting of [1.1.]-bicyclopentane, cyclobutyl, and cyclopropyl;

p is 0, 1, or 2; and each $R^B$ group (when present) is independently selected from the group consisting of fluoro, —CN, and —OMe.

In an alternative of the immediately preceding embodiment, m is 0. In another alternative of the immediately preceding embodiment, m is 1. In another alternative of the immediately preceding embodiment, m is 2.

In another alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):
n=1;
-$L_1$- is —CH$_2$O—:
ring A is phenyl;
m is 0, 1, or 2;
each $R^A$ (when present) is fluoro; and
ring B is cyclopropyl;

In an alternative of the immediately preceding embodiment, m is 0. In another alternative of the immediately preceding embodiment, m is 1. In another alternative of the immediately preceding embodiment, m is 2.

In one embodiment, in each of Formulas (I), (I'), (IA), and (IA'):
n=1;
-$L_1$- is a bond:
ring B is selected from the group consisting of benzimidazolyl, benzoisothiazolyl, benzoisoxazolyl, benzothiazolyl, benzoxazolyl, cyclopropyl, dihydroindenyl, dihydrooxazolyl, furanyl, imidazolyl, imidazopyridinyl, imidazopyrimidinyl, imidazothiazolyl, indenyl, indolyl, isothiazolyl, isoxazolyl, oxadiazolyl, oxazolyl, phenyl, pyrazinyl, pyrazolyl, pyrazolopyridinyl, pyrazolopyrimidinyl, pyridazinyl, pyridinyl, pyrimidinyl, pyrazolopyridinyl, pyrrolidinyl, pyrrolyl, pyrrolopyridinyl, pyrrolopyrimidinyl, tetrazolyl, thiadiazolyl, thiazolyl, thienyl, thienylpyridine, and triazolyl;
p is 0, 1, 2, or 3, with the proviso that the value of p does not exceed the number of available substitutable hydrogen atoms on ring B; and
each $R^B$ group (when present) is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, and —OCH$_2$CH$_2$F.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):
n=1;
-$L_1$- is a bond;
ring B is selected from the group consisting of imidazopyridinyl, imidazopyrimidinyl, indolyl, isothiazolyl, isoxazolyl, oxadiazolyl, oxazolyl, phenyl, pyrazinyl, pyrazolyl, pyrazolopyridinyl, pyrazolopyrimidinyl, pyridinyl, pyrimidinyl, pyrazolopyridinyl, pyrrolyl, pyrrolopyridinyl, pyrrolopyrimidinyl, thiadiazolyl, thiazolyl, thienyl, and triazolyl;
p is 0, 1, 2, or 3, with the proviso that the value of p does not exceed the number of available substitutable hydrogen atoms on ring B; and
each $R^B$ group (when present) is independently selected from the group consisting of fluoro, chloro, —CN, —OCH$_3$, —O—CH$_2$-cyclopropyl, —OCH$_2$—C≡C—H, —OCH$_2$—C≡C—CH$_3$ methyl, ethyl, cyclopropyl, —CH$_2$-cyclopropyl, —CH$_2$OCH$_3$, —C≡CH, —C≡C—CH, —CF$_3$, —CHF$_2$, —OCF$_3$, —OCHF$_2$.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):
n=1;
-$L_1$- is a bond;
ring B is selected from the group consisting of phenyl, pyridinyl, and pyrimidinyl;
p is 0, 1, or 2; and
each $R^B$ group (when present) is independently selected from the group consisting of fluoro, chloro, methyl, —CN, —OMe, —C≡CH, —C≡C—CH$_3$, —CHF$_2$.

In an alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):
n=1;
-$L_1$- is a bond:
ring A is selected from the group consisting of phenyl, pyridinyl, and thienyl:
m is 0, 1, 2, or 3;
each $R^A$ (when present) is independently selected from the group consisting of fluoro, chloro, methyl, and —CHF$_2$;
ring B is selected from the group consisting of phenyl, pyridinyl, and pyrimidinyl: p is 0, 1, or 2; and
each $R^B$ group (when present) is independently selected from the group consisting of fluoro, chloro, methyl, —CN, —OMe, —C≡CH, —C≡C—CH$_3$, —CHF$_2$.

In an alternative of the immediately embodiment, m is 0. In another alternative of the immediately preceding embodiment, in is 1. In another alternative of the immediately preceding embodiment, m is 2. In another alternative of the immediately preceding embodiment, m is 3.

In another alternative of the immediately preceding embodiment, p is 0. In another alternative of the immediately preceding embodiment, p is 1. In another alternative of the immediately preceding embodiment, p is 2.

In some embodiments, in each of Formulas (I), (I'), (IA), and (IA'):
n is 0. In these embodiments, the moiety:

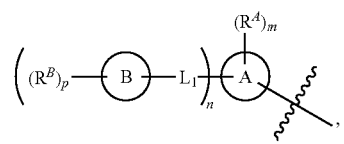

, has the form:

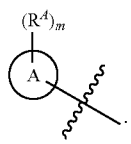

In one embodiment, in each of Formulas (I), (I'), (IA), and (IA'):
n=0;
ring A is selected from the group consisting of phenyl, pyridazinyl, pyridinyl, pyrimidinyl, pyrazinyl, pyrazolyl, triazinyl, thiazolyl, and thienyl;
m is 0, 1, 2, 3, or 4, with the proviso that the value of m does not exceed the number of available substitutable hydrogen atoms on ring A; and
each $R^A$ (when present) is independently selected from the group consisting of fluoro, chloro, bromo, oxo, —OH, —CN, methyl, ethyl, propyl, butyl, cyclopropyl, —CH$_2$OCH$_3$, —CH$_2$OCF$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$NHCH$_2$CF$_3$, —CF$_3$, —CHF$_2$, —CH$_2$F, —OCH$_3$, —OCH$_2$CH$_3$, —OCH$_2$CH$_2$CH$_3$, —OCH$_2$CH(CH$_3$)$_2$, —OCH$_2$CH$_2$OCH$_3$, —OCF$_3$, —OCHF$_2$, —OCH$_2$F, —OCH$_2$CF$_3$, —OCH$_2$CHF$_2$, —OCH$_2$CH$_2$F, and —OCH$_2$CH$_2$CF$_3$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3, with the proviso that the value of m does not exceed the number of available substitutable hydrogen atoms on ring A. In another alternative of the immediately preceding embodiment, m is 4, with the proviso that the value of m does not exceed the number of available substitutable hydrogen atoms on ring A.

In one embodiment, in each of Formulas (I), (I'), (IA), and (IA'):
n=0:
ring A is selected from the group consisting of phenyl and pyridinyl;
m is 0, 1, 2, or 3; and
each $R^A$ (when present) is independently selected from the group consisting of fluoro, bromo, oxo, —OH, —CN, methyl, ethyl, cyclopropyl, —CH$_2$OCH$_3$, —CH$_2$OCF$_3$, —CH$_2$NHCH$_2$CH$_3$, —CH$_2$NHCH$_2$CF$_3$, —CF$_3$, —CHF$_2$, —CH$_2$F, —OCH$_3$, —OCH$_2$CH(CH$_3$)$_2$, —OCH$_2$CH$_2$OCH$_3$, —OCF$_3$, —OCHF$_2$, —OCH$_2$CF$_3$, —OCH$_2$CHF$_2$, and —OCH$_2$CH$_2$CF$_3$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3

In one embodiment, in each of Formulas (I), (I'), (IA), and (IA'):
n=0:
ring A is selected from the group consisting of phenyl and pyridinyl:
m is 0, 1, 2, or 3; and
each $R^A$ (when present) is independently selected from the group consisting of fluoro, bromo, —CH$_2$NHCH$_2$CF$_3$, —OCH$_3$, and —OCH$_2$CH(CH$_3$)$_2$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), and (IA'):
n=0:
ring A is phenyl:
m is 0, 1, or 2; and
each $R^A$ (when present) is independently selected from the group consisting of fluoro, bromo, —OCH$_3$, and —OCH$_2$CH(CH$_3$)$_2$.

In an alternative of the immediately preceding embodiment, m is 0. In another alternative of the immediately preceding embodiment, m is 1. In another alternative of the immediately preceding embodiment, m is 2.

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

Specific non-limiting examples of compounds of the invention are shown in the table of examples below. While only one tautomeric form of each compound is shown in the tables, it shall be understood that both tautomeric forms of the compounds are contemplated as being within the scope of the non-limiting examples.

In another embodiment, in each of Formulas (I), (I'), (IA), and (IA'), 1 to 3 carbon atoms of the compounds of the invention may be replaced with 1 to 3 silicon atoms so long as all valency requirements are satisfied.

Another embodiment provides a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents which may be useful in combination with the compounds of the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis A1, (c) drugs that may be useful for treating neurodegenerative diseases, and (d) drugs that may be useful for the treatment of type II diabetes and/or one or more symptoms or associated pathologies thereof.

Non-limiting examples of additional therapeutic agents which may be useful in combination with the compounds of the invention include drugs that may be useful for the treatment, prevention, delay of onset, amelioration of any pathology associated with A$\beta$ and/or a symptom thereof. Non-limiting examples of pathologies associated with A$\beta$ include: Alzheimer's Disease. Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"). Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, $\beta$-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Non-limiting examples of additional therapeutic agents for that may be useful in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)): cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators: gamma secretase inhibitors; non-steroidal anti-inflammatory agents: anti-inflammatory agents that can reduce neuroinflammation: anti-amyloid antibodies (such as bapineuzemab, Wyeth/Elan); vitamin E; nicotinic acetylcholine receptor agonists; CB1 receptor inverse agonists or CB1 receptor antagonists: antibiotics: growth hormone secretagogues: histamine H3 antagonists: AMPA agonists: PDE4 inhibitors: GABA$_A$ inverse agonists; inhibitors of amyloid aggregation; glycogen synthase kinase beta inhibitors: promoters of alpha secretase activity: PDE-10 inhibitors; Tau kinase inhibitors (e.g., GSK3beta inhibitors, cdk5 inhibitors, or ERK inhibitors): Tan aggregation inhibitors (e.g., Rember®): RAGE inhibitors (e.g., TTP 488 (PF-4494700)): anti-Abeta vaccine; APP ligands; agents that upregulate insulin, cholesterol lowering agents such as HMG-CoA reductase inhibitors (for example, statins such as Atorvastatin. Fluvastatin, Lovastatin, Mevastatin, Pitavastatin, Pravastatin. Rosuvastatin. Simvastatin) and/or cholesterol absorption inhibitors (such as Ezetimibe), or combinations of HMG-CoA reductase inhibitors and cholesterol absorption inhibitors (such as, for example, Vytorin®): fibrates (such as, for example, clofibrate, Clofibride, Etofibrate, and Aluminium Clofibrate); combinations of fibrates and cholesterol lowering agents and/or cholesterol absorption inhibitors: nicotinic receptor agonists; niacin; combinations of niacin and cholesterol absorption inhibitors and/or cholesterol lowering agents (e.g., Simcor® (niacin/simvastatin, available from Abbott Laboratories, Inc.): LXR agonists: LRP mimics: H3 receptor antagonists: histone deacetylase inhibitors: hsp90 inhibitors; 5-HT4 agonists (e.g., PRX-03140 (Epix Pharmaceuticals)): 5-HT6 receptor antagonists; mGluR1 receptor modulators or antagonists: mGluR5 receptor modulators or antagonists: mGluR2/3 antagonists: Prostaglandin EP2 receptor antagonists: PAI-1 inhibitors: agents that can induce Abeta efflux such as gelsolin: Metal-protein attenuating compound (e.g. PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention or pharmaceutically acceptable salt thereof, and a pharmaceutically acceptable carrier or diluent.

Another embodiment provides a method of inhibiting $\beta$-secretase comprising exposing a population of cells expressing $\beta$-secretase to at least one compound of the invention, or a tautomer thereof, in an amount effective to inhibit $\beta$-secretase. In one such embodiment, said population of cells is in vivo. In another such embodiment, said population of cells is ex vivo. In another such embodiment, said population of cells is in vitro.

Additional embodiments in which the compounds of the invention may be useful include: a method of inhibiting $\beta$-secretase in a patient in need thereof. A method of inhibiting the formation of A$\beta$ from APP in a patient in need thereof. A method of inhibiting the formation of A$\beta$ plaque and/or A$\beta$ fibrils and/or A$\beta$ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer thereof, or pharmaceutically acceptable salt of said compound or said tautomer, in a therapeutically effective amount to inhibit said pathology or condition in said patient.

Additional embodiments in which the compounds of the invention may be useful include: a method of treating, preventing, and/or delaying the onset of one or more pathologies associated with A$\beta$ and/or one or more symptoms of one or more pathologies associated with A$\beta$. Non-limiting examples of pathologies which may be associated with A$\beta$ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"). Parkinson's disease, and/or Down's syndrome, dementia, stroke, microgliosis and brain inflammation, pre-senile dementia, senile dementia, dementia associated with Alzheimer's disease. Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, said method(s) comprising administering to said patient in need thereof at least one compound of the invention, or a tautomer thereof, or pharmaceutically acceptable salt of said compound or said tautomer, in an amount effective to inhibit said pathology or pathologies.

Another embodiment in which the compounds of the invention may be useful includes a method of treating Alzheimer's disease, wherein said method comprises administering an effective (i.e., therapeutically effective) amount of one or more compounds of the invention (or a tautomer thereof, or pharmaceutically acceptable salt of said compound or said tautomer), optionally in further combination with one or more additional therapeutic agents which may be effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

Another embodiment in which the compounds of the invention may be useful includes a method of treating mild cognitive impairment ("MCI"), wherein said method comprises administering an effective (i.e., therapeutically effective) amount of one or more compounds of the invention (or a tautomer thereof, or pharmaceutically acceptable salt of said compound or said tautomer) to a patient in need of treatment. In one such embodiment, treatment is commenced prior to the onset of symptoms.

Another embodiment in which the compounds of the invention may be useful includes a method of preventing, or alternatively of delaying the onset, of mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several years before, an effective (i.e., therapeutically effective), and over a period of time and at a frequency of dose sufficient for the therapeutically effective degree of inhibition of the BACE enzyme over the period of treatment, an amount of one or more compounds of the invention (or a tautomer thereof, or pharmaceutically acceptable salt of said compound or said tautomer) to a patient in need of treatment.

Another embodiment in which the compounds of the invention may be useful includes a method of treating Down's syndrome, comprising administering an effective (i.e., therapeutically effective) amount of one or more compounds of the invention (or a tautomer thereof, or pharmaceutically acceptable salt or solvate of said compound or said tautomer) to a patient in need of treatment.

Another embodiment in which the compounds of the invention may be useful includes a kit comprising, in separate containers, in a single package, pharmaceutical compositions for use in combination, wherein one container comprises an effective amount of a compound of the invention (or a tautomer thereof, or pharmaceutically acceptable salt of said compound or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1 and/or BACE-2.

In various embodiments, the compositions and methods disclosed above and below wherein the compound(s) of the invention is a compound or compounds selected from the group consisting of the exemplary compounds of the invention described herein.

In another embodiment, the invention provides methods of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease. Such methods comprise administering a compound of the invention, or a pharmaceutically acceptable salt thereof, to a patient in need thereof in an amount effective to treat said disease or pathology.

In another embodiment, the invention provides for the use of any of the compounds of the invention for use as a medicament, or in medicine, or in therapy.

In another embodiment, the invention provides for use of a compound of the invention for the manufacture of a medicament for the treatment of a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" protion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine (F), chlorine (Cl), bromine (Br), or iodine (I). Preferred are fluorine, chlorine and bromine.

"Alkyl" means an aliphatic hydrocarbon group, which may be straight or branched, comprising 1 to 10 carbon atoms. "Lower alkyl" means a straight or branched alkyl group comprising 1 to 4 carbon atoms. Branched means that one or more lower alkyl groups such as methyl, ethyl or propyl, are attached to a linear alkyl chain. Non-limiting examples of suitable alkyl groups include methyl (Me), ethyl (Et), n-propyl, isopropyl, n-butyl, i-butyl, and t-butyl.

"Alkenyl" means an aliphatic hydrocarbon group containing at least one carbon-carbon double bond and which may be straight or branched and comprising 2 to 10 carbon atoms in the straight or branched chain. Branched means that one or more lower alkyl groups such as methyl, ethyl propyl, ethenyl or propenyl are attached to a linear or branched alkenyl chain. "Lower alkenyl" means 2 to 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising 2 to 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means 2 to 4 carbon atoms in the chain which may be straight or branched. Non-limiting examples of suitable alkynyl groups include ethynyl, propynyl. 2-butynyl and 3-methylbutynyl.

"Aryl" means an aromatic monocyclic or multicyclic ring system comprising 6 to 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolnyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moities include pyridyl, pyrazinyl, furanyl, thienyl, pyrimidinyl, pyridazinyl, pyridonyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

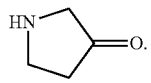

As used herein, the term "monocyclic heterocycloalkyl" refers to monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

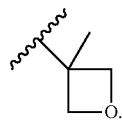

It should be noted that in hetero-atom containing ring systems of this invention, there are no hydroxyl groups on carbon atoms adjacent to a N, O or S, as well as there are no N or S groups on carbon adjacent to another heteroatom.

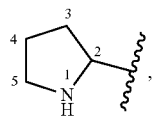

there is no —OH attached directly to carbons marked 2 and 5.

"Alkoxy" means an —O-alkyl group in which the alkyl group is as previously described. Non-limiting examples of alkoxy groups include methoxy, ethoxy, n-propoxy, isopropoxy and n-butoxy. The bond to the parent moiety is through the oxygen.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^6$ in —N($R^6$)$_2$, or a variable appears more than once in a structure presented herein, the variables can be the same or different.

The line —, as a bond generally indicates a mixture of, or either of, the possible isomers, e.g., containing (R)- and (S)-stereochemistry. For example:

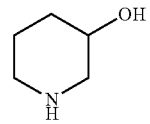

means containing both

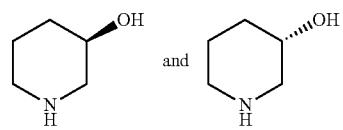

The wavy line ～～～, as used herein, indicates a point of attachment to the rest of the compound. Lines drawn into the ring systems, such as, for example:

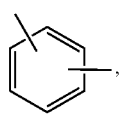

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

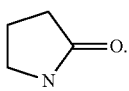

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

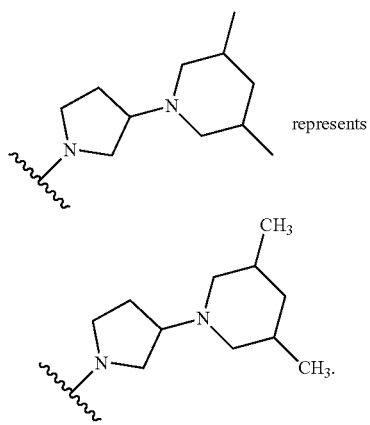

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991). Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates.) and the like. Additionally, acids which are generally considered suitable for the formation of pharmaceutically useful salts from basic pharmaceutical compounds are discussed, for example, by P. Stahl et al, Camille G, (eds.) *Handbook of Pharmaceutical Salts. Properties, Selection and Use*. (2002)

Zurich: Wiley-VCH: S. Berge et al, *Journal of Pharmaceutical Sciences* (1977) 66(1) 1-19: P. Gould, *International J of Pharmaceutics* (1986) 33 201-217: Anderson et al, *The Practice of Medicinal Chemistry* (1996), Academic Press, New York; and in The Orange Book (Food & Drug Administration, Washington. D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl): (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention. Thus, compounds of the invention conforming to the formula:

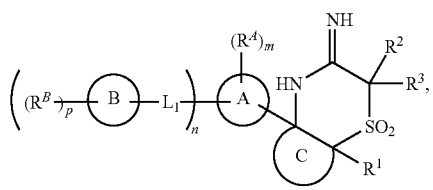

and its tautomer, which can be depicted as:

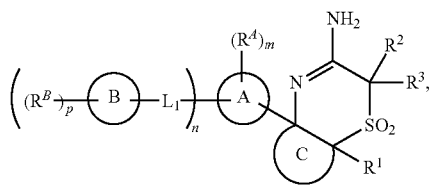

are both contemplated as being within the scope of the compounds of the invention. As noted above, while only one said tautomeric form of each example compound of the invention may be shown in the tables and appended claims, it shall be understood that both of these tautomeric forms of the compounds are contemplated as being within the scope of the non-limiting example compounds of the invention.

The compounds of the invention may contain asymmetric or chiral centers, and, therefore, exist in different stereoisomeic forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comparing one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for such monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by the following abbreviations:

Acetic acid: AcOH
Acetonitrile: MeCN
Aqueous: aq.
[2-(Di-1-adamantylphosphino)-2',4',6'-triisopropyl-3,6-dimethoxybiphenyl][2-(2'-amino-1,1'-biphenyl)]palladium (II) methanesulfonate: AdBrettPhos Pd G3 or Di-Ad-BrettPhos-G3-Palladacycle
4,5-Bis(diphenylphosphino)-9,9-dimethylxanthene: Xantphos
Boc-anhydride: (Boc)$_2$O
tert-Butoxycarbonyl: t-Boc or Boc
tert-Butyl: t-Bu or tBu
n-Butyllithium: nBuLi or n-BuLi
Dichloromethane: DCM
Diethylamine: DEA
Diisopropylazodicarboxylate: DIAD
Diisopropylethylamine: DIEA, DIPEA or iPr$_2$NEt
Dimethylacetamide: DMA
Dimethylformamide: DMF
Dimethylsulfoxide: DMSO
Ethyl: Et
1-Ethyl-3-(3-dimethylaminopropyl)carbodiimide: EDCI
Diethylether: Et$_2$O
Equivalent: eq
Ethanol: EtOH
Ethyl acetate: AcOEt, EtOAc, or EA
Example: Ex.
Grams: g
Hexanes: hex
High performance liquid chromatography: HPLC
Inhibition: Inh.
iso-propyl alcohol: IPA
Lithium bis(trimethylsilyl)amide: LiHMDS
Liquid chromatography mass Spectrometry: LCMS
Methyl: Me
Methanol: MeOH
N-methylpyrrolidinone: NMP
Microliters: μl or μL
Micrometers or microns: um or μm
Milligrams: mg
Milliliters: mL
Millimeters: mm
Millimoles: mmol
Minutes: min
Molar: M
Nanomolar: nM
Normal (concentration): N
Nuclear magnetic resonance spectroscopy: NMR
Number: No, or no, or #
Observed: Obs.
Petroleum ether: PE
Preparative high performance liquid chromatography: p-HPLC
Preparative thin layer chromatography: p-TLC
Potassium bis(trimethylsilyl)amide: KHMDS
Room temperature (ambient, about 25° C.): rt or RT Saturated: sat.
Silica gel: SiO$_2$
Supercritical Fluid Chromatography: SFC
Tetramethyl(tris(dimethylamino)phosphoranylidene)phosphorictriamid-Et-inin: Phosphazene base P2-Et
Temperature: temp.
Triethylamine: Et$_3$N, TEA
Trifluoroacetic acid: TFA
Tetrahydrofuran: THF Method A

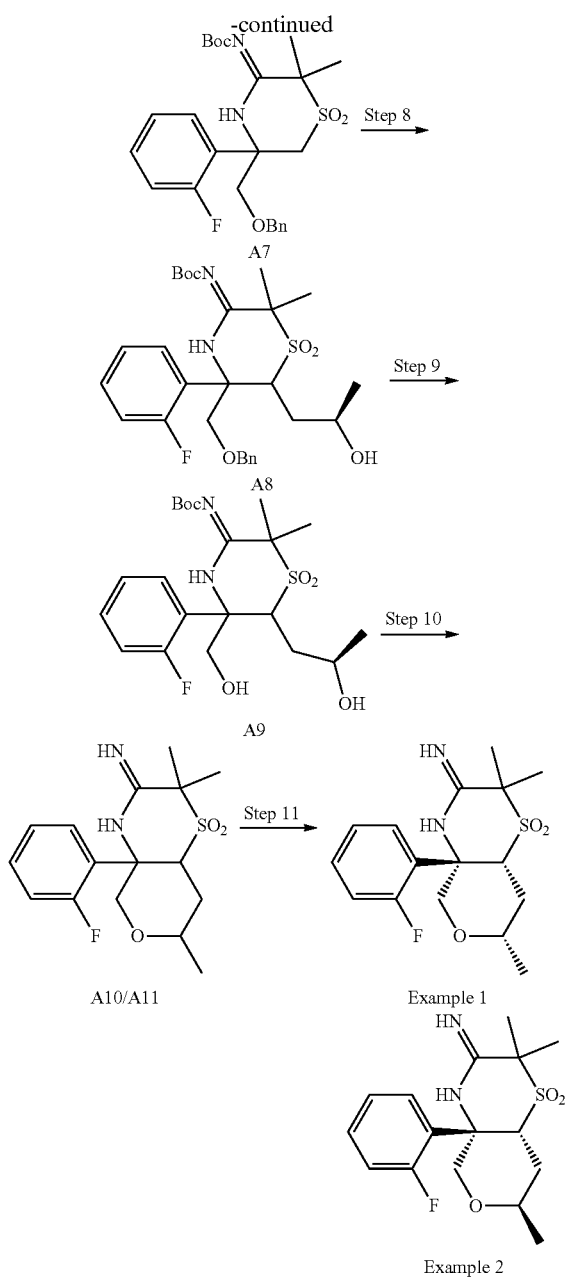

Step 1

To a solution of 2-(benzyloxy)acetic acid (3.23 g, 19.5 mmol) in DCM (60 mL) was added EDCI (6.1 g, 29.2 mmol), followed by N,O-dimethylhydroxylamine hydrochloride (2.8 g, 29.2 mmol) and pyridine (10 mL). The mixture was stirred at 25° C. for 16 h, then washed with 0.1 M aq. HCl, brine, dried (Na₂SO₄), and concentrated. The residue was purified by silica gel chromatography (PE:EA=10:1) to afford A1.

Step 2

To a solution of 1-bromo-2-fluorobenzene (47.7 g, 273 mmol) in THF (500 mL) at −78° C. was added n-BuLi (2.5 M in hexane, 109 mL, 273 mmol) in a dropwise fashion. The resulting solution was stirred at −78° C. for 1 h, whereupon a solution of compound A1 (47.5 g, 227 mmol) in THF (50 mL) was slowly added. The resulting mixture was stirred at −78° C. for 1 h, then quenched by the addition of 150 mL of saturated aq. NH₄Cl (150 mL) and water (1 L). The mixture was extracted with EtOAc, and then the combined organic phases were washed with water, brine, dried (Na₂SO₄), and evaporated. The residue was purified by silica gel chromatography (PE:EA=20:1) to afford A2.

Step 3

A solution of A2 (5.8 g, 23.8 mmol), (R,S)-tert-butylsulfinamide (4.4 g, 35.7 mmol) and Ti(OEt)₄ (16.3 g, 71.4 mmol) in THF (60 mL) was stirred at 25° C. under N₂ for 16 h. The reaction mixture was quenched by the addition of ice-water and then filtered. The filtrate was extracted with EtOAc, and then the combined extracts were washed with water, brine, dried (Na₂SO₄), and concentrated. The residue was purified by silica gel chromatography (PE:EA=15:1) to afford A3.

Step 4

To a solution of 2-methyl-2-(methylsulfonyl)propanenitrile (13.3 g, 91 mmol) in THF (250 mL) at −78° C. was added n-BuLi (2.5 M in hexane, 36 mL, 91 mmol). The mixture was stirred at −78° C. for 1 h, whereupon a solution of compound A3 (21 g, 61 mmol) in THF (50 mL) was added. The resulting mixture was stirred at −78° C. for 3 h, quenched with saturated aq. NH₄Cl, and extracted with EtOAc. The combined extracts were washed with brine, dried (Na₂SO₄), and concentrated. The residue was purified by silica gel chromatography (PE:EA=3:1) to afford A4.

Step 5

To a solution of compound A4 (16 g, 41 mmol) in DCM (150 mL) at 0° C. was added HCl (4M in dioxane, 30 mL). The cooling bath was removed and the solution was allowed to warm to 25° C., and then stirred for 1 h. The reaction mixture was concentrated and the resulting residue was dissolved in DCM and washed with aq. NaHCO₃. The organic layer was dried (Na₂SO₄), concentrated and A5 was used in the next step without further purification.

Step 6

A suspension of A5 (8.7 g, 22 mmol) and CuCl (4.4 g, 44 mmol) in EtOH (170 mL) was stirred at 70° C. for 14 h. The mixture was concentrated, and then diluted with 1 N aq. NaOH (200 mL), and filtered. The filtrate was extracted with DCM and the combined extracts were washed with brine, dried (Na₂SO₄), concentrated and purified by silica gel chromatography (PE:EA=2:1) to afford A6.

Step 7

To a solution of A6 (23 g, 58.9 mmol) in DCM (250 mL) were added triethylamine (8.94 g, 88 mmol) and di-tert-butyl dicarbonate (15.4 g, 70.7 mmol). The mixture was stirred at 25° C. for 16 h, then diluted with water (80 mL) and extracted with EtOAc (3×200 mL). The organic extracts were dried over Na₂SO₄, filtered and concentrated. The residue was purified by silica gel chromatography (PE/ethyl acetate=20:1 to 5:1) to afford A7.

Step 8

To a stirred solution of A7 (500 mg, 1.02 mmol) in THF (8 mL) at −20° C. under N₂ was added lithium bis(trimethylsilyl)amide (1 M in THF, 4.08 mL, 4.08 mmol). After 1 h, (R)-2-methyloxirane (118 mg, 2.04 mmol) in THF (4 mL) was added into the mixture. The mixture was then warmed and stirred at 25° C. for 3 h. It was quenched with saturated NH₄Cl (15 mL), extracted with EtOAc (3×20 mL). The organic extracts were dried over Na₂SO₄ and concentrated. The residue was purified by silica gel chromatography (PE/ethyl acetate=20:1 to 3:1) to afford A8.

Step 9

To a solution of A8 (2.0 g, 3.08 mmol) in MeOH (30 mL) were added 20% dihydroxypalladium on carbon (2.165 g, 3.08 mmol), followed by HCl (4 M in dioxane, 0.6 mL, 2.40 mmol). The mixture was stirred under 50 psi of H2 at 45° C. for 14 h, filtered, washed with MeOH (3×20 mL). The filtrate was concentrated in vacuo to a volume of ~30 mL. To the solution were added 1 eq Pd(OH)$_2$ (20%) and 0.6 mL 4 M HCl in dioxane. The mixture was stirred at 45° C. under 50 psi of H$_2$ for 18 h. The mixture was filtered, washed with MeOH (3×30 mL) and the filtrate was concentrated in vacuo to give crude A9.

Step 10

A mixture of A9 (500 mg, 1.09 mmol) and concentrated HCl (40 mL, 480 mmol) was heated at 110° C. for 48 h. The mixture was cooled and then neutralized with saturated aq. Na$_2$CO$_3$ to pH 8 and extracted with DCM (3×50 mL). The combined organic extracts were dried over Na$_2$SO$_4$, filtered and concentrated in vacuo. The residue was purified by p-HPLC to give two fractions A10 and A11.

Step 11

Fraction A10 (100 mg, 0.29 mmol) was purified by SFC (Chiralcel OJ-3 150×4.6 mm, 3 um) and then purified by p-HPLC to give Example 1. Fraction A11 was purified by SFC (Chiralcel OD: 250 mm×30 mm. 5 um) and then purified by p-HPLC to give Example 2.

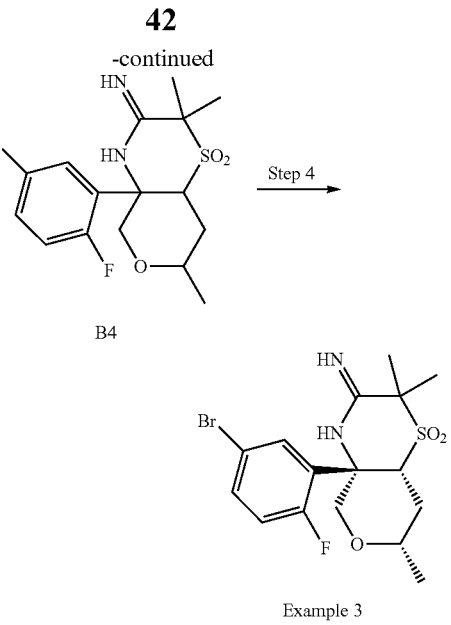

B4

Example 3

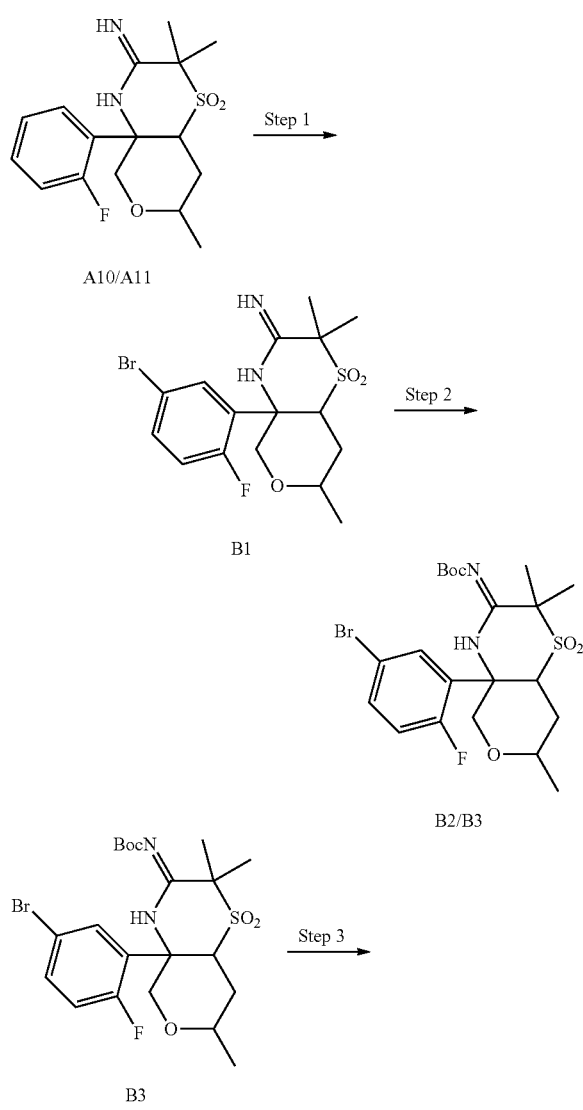

Method B

A10/A11

B1

B2/B3

B3

Step 1

To a stirred solution of a mixture of fractions A10 and A11 (1.21 g, 3.55 mmol) in acetonitrile (7 mL) cooled with an ice bath were added 1,3-dibromo-5,5-dimethylimidazolidine-2,4-dione (1.52 g, 5.33 mmol), followed by concentrated sulfuric acid (1.14 mL, 21.3 mmol) slowly with the internal temperature of the reaction monitored and maintained below 20° C. Upon completion of addition, the mixture was warmed and stirred at 20° C. for 10 min and at 55° C. for 2 h. The mixture was poured into ice-water (150 mL), neutralized with saturated aq. NaHCO$_3$ to pH 7 and extracted with EtOAc (3×100 mL). The combined extracts were dried over Na$_2$SO$_4$, filtered and concentrated in vacuo to give crude B1, which was used in the next step directly.

Step 2

To a solution of B1 (3.0 g, 5.6 mmol) in DCM (40 mL) were added Boc$_2$O (1.94 mL, 8.37 mmol) and triethylamine (2.33 mL, 16.7 mmol). The mixture was stirred at 20° C. for 13 h. Additional 0.5 eq Boc$_2$O and 1 eq Et$_3$N were added, the mixture was stirred at 20° C. for another 13 h. It was concentrated in vacuo; the residue was purified by silica gel chromatography (PE/EtOAc=20:1 to 5:1) to give crude product, which was separated by SFC (Chiralcel OD-3: 150×4.6 mm, 3 um) to give two fractions B2 and B3.

Step 3

To a solution of B3 (30 mg, 0.058 mmol) in DCM (2 mL) was added TFA (0.5 mL, 6.49 mmol). The mixture was stirred at 20° C. for 1 h and concentrated. The residue was purified by p-HPLC to give B4.

Step 4

Compound B4 (30 mg, 0.072 mmol) was subjected to SFC purification (Chiralpak AD-3 150×4.6 mm, 3 um) to give Example 3.

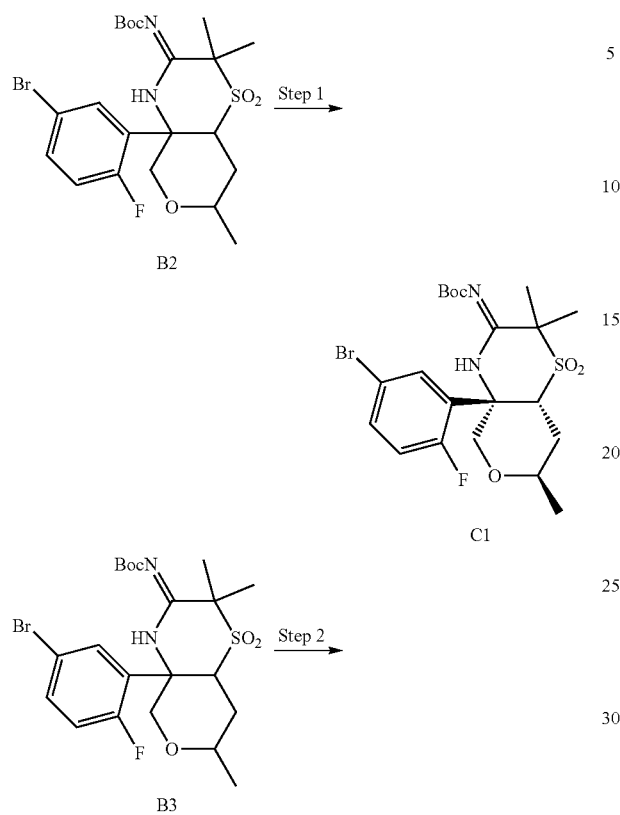

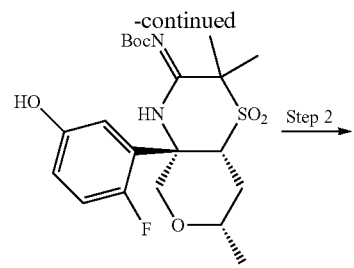

D1

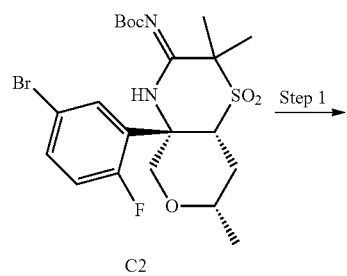

Method C

B2

C1

B3

C2

Step 1

Fraction B2 (0.85 g, 1.64 mmol) was separated by SFC (Whelk-01 250 mm×30 mm, 10 µm) to give C1.

Step 2

Fraction B3 (0.9 g, 1.7 mmol) was separated by SFC (Chiralpak AD-3 150×4.6 mm, 3 um) to give C2.

Method D

C2

D2

Example 4

Step 1

A mixture of compound $C_2$ (350 mg, 0.67 mmol) and AdBrettphos Pd G3 (102 mg, 0.101 mmol) in DMSO (5 mL) was purged with nitrogen for 3 min. To the mixture were added water (0.073 mL, 4.04 mmol) and Phosphazene base P2-Et (800 mg, 2.358 mmol). The mixture was purged with nitrogen for 3 min and stirred at 20° C. for 15 h. Additional 0.03 eq of the precatalyst was added and purged with nitrogen for 3 min, and then 3.5 eq of the base and 6 eq of water were added. The mixture was purged with nitrogen for 3 min and stirred for 48 h. The mixture was partitioned between water (80 mL) and EtOAc (30 mL). The aqueous layer was extracted with EtOAc (3×30 mL). The combined extracts were dried over $Na_2SO_4$, filtered and concentrated in vacuo. The residue was purified by silica gel chromatography (PE/ethyl acetate=10:1~3:1) to afford D1.

Step 2

A mixture of D1 (79 mg, 0.173 mmol), 1-bromo-2-methylpropane (71.1 mg, 0.519 mmol) and $K_2CO_3$ (71.7 mg, 0.519 mmol) in DMF (1 mL) was stirred at 20° C. for 14 h. Additional 3 eq 1-bromo-2-methylpropane and 3 eq $K_2CO_3$ were added and the mixture was stirred at 20° C. for 14 h. It was partitioned between water (30 mL) and EtOAc (20 mL). The aqueous layer was extracted with EtOAc (3×20 mL). The combined extracts were dried over $Na_2SO_4$, filtered and concentrated in vacuo to give crude D2, which was used in the next step directly.

Step 3

To a solution of D2 (80 mg, 0.16 mmol) in DCM (1.5 mL) was added trifluoroacetic acid (0.361 mL, 4.68 mmol) dropwise. The mixture was stirred at 20° C. for 1 h. It was neutralized with saturated aq. $NaHCO_3$ to pH 7, partitioned between water (30 mL) and DCM (15 mL). The aqueous layer was extracted with DCM (3×15 mL). The combined extracts were dried over Na₂SO₄, filtered and concentrated in vacuo. The residue was purified by p-HPLC to give Example 4.

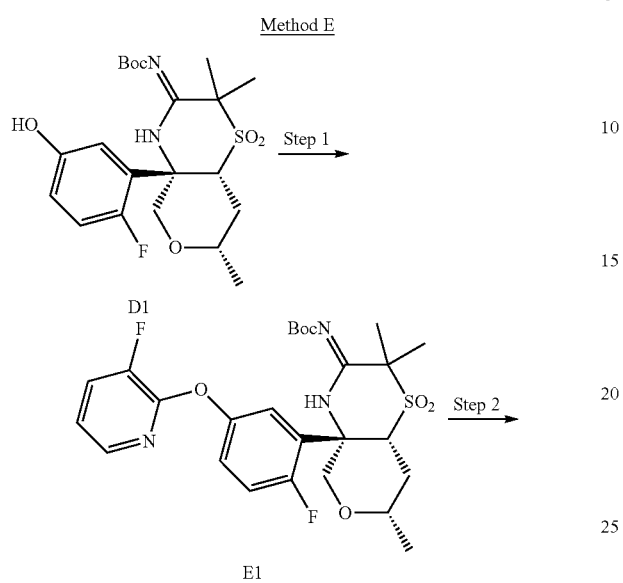

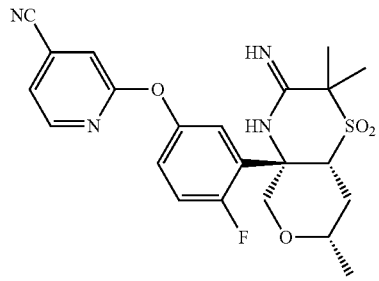 [SMILES: C[C@H]1C[C@@H]2[C@](c3cc(Oc4cc(C#N)ccn4)ccc3F)(CO1)NC(=N)C(C)(C)S2(=O)=O]

Example 6

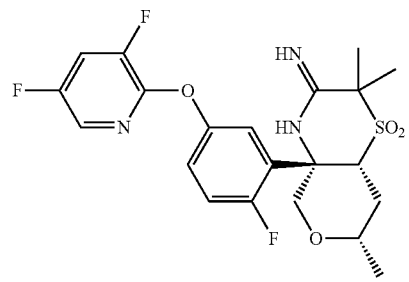 [SMILES: C[C@H]1C[C@@H]2[C@](c3cc(Oc4ncc(F)cc4F)ccc3F)(CO1)NC(=N)C(C)(C)S2(=O)=O]

Example 7

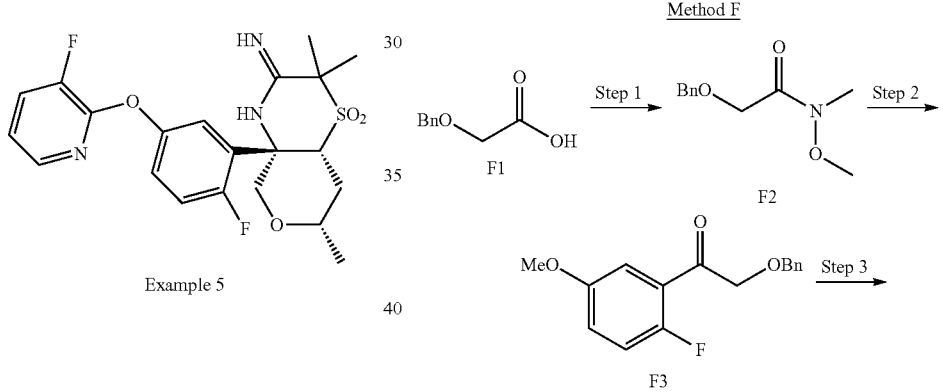

Step 1

A mixture of compound D1 (80 mg, 0.175 mmol). 2,3-difluoropyridine (60.5 mg, 0.526 mmol) and cesium carbonate (171 mg, 0.526 mmol) in DMSO (4 mL) was stirred at 60° C. for 1 h. It was partitioned between water (50 mL) and EtOAc (20 mL). The aqueous layer was extracted with EtOAc (3×20 mL). The combined extracts were dried over Na₂SO₄, filtered and concentrated in vacuo to give E1.

Step 2

To a solution of E1 (100 mg, 0.181 mmol) in DCM (2 mL) was added TFA (0.419 mL. 5.44 mmol) dropwise. The mixture was stirred at 20° C. for 1 h, neutralized with saturated aq. NaHCO₃ to pH 7. It was partitioned between water (30 mL) and DCM (15 mL): the aqueous layer was extracted with DCM (3×15 mL). The combined extracts were dried over Na₂SO₄, filtered and concentrated in vacuo. The residue was purified by p-HPLC to give Example 5.

Examples 6 and 7 were prepared from intermediate D1 similarly using the appropriate alternative to 2,3-difluoropyridine in Step 1.

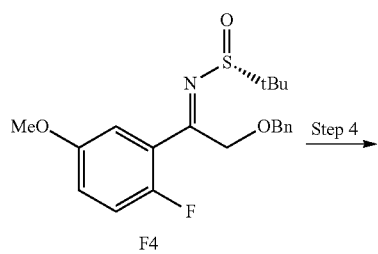

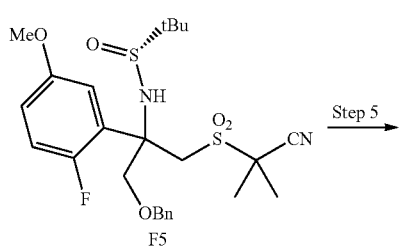

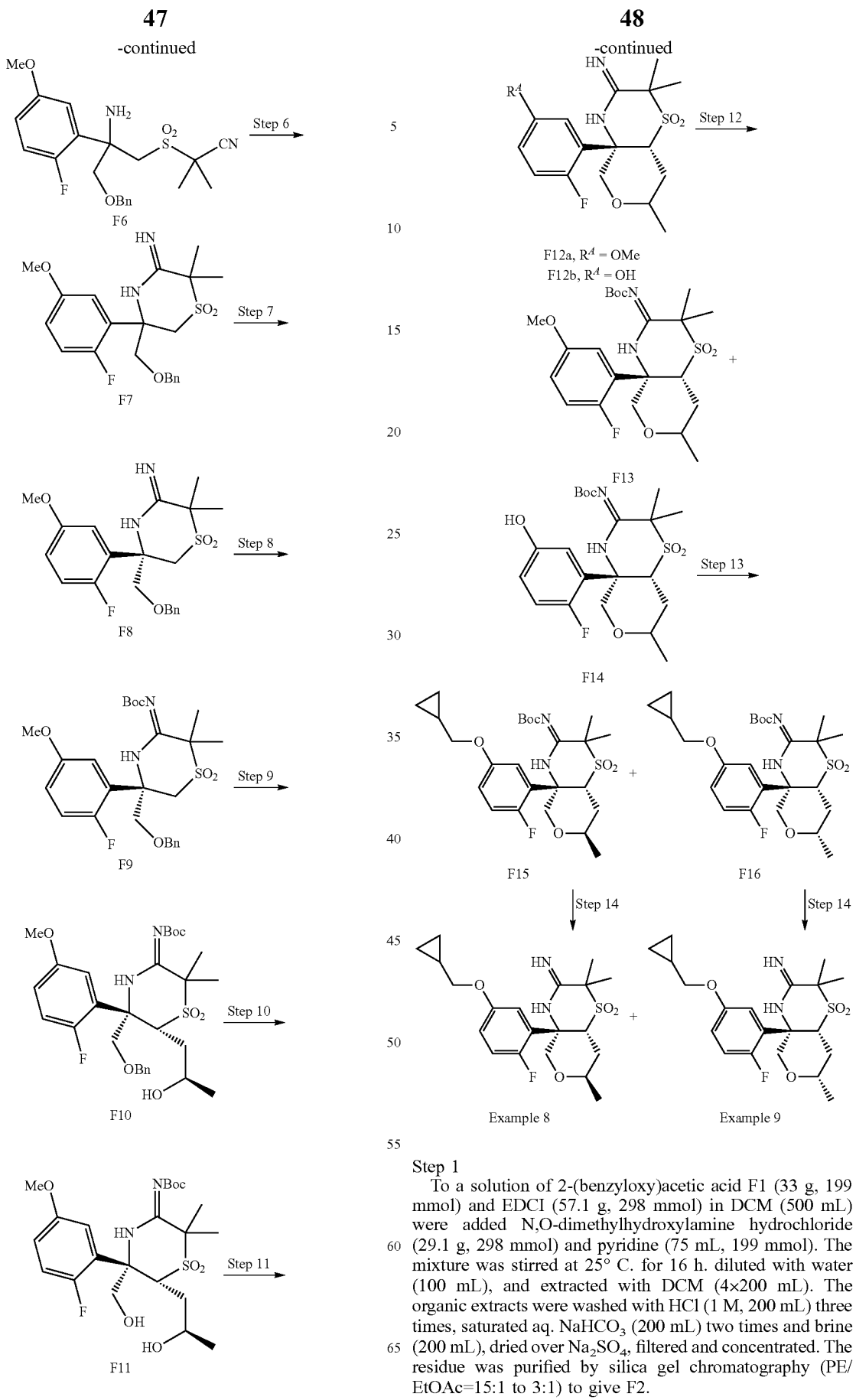

Step 1

To a solution of 2-(benzyloxy)acetic acid F1 (33 g, 199 mmol) and EDCI (57.1 g, 298 mmol) in DCM (500 mL) were added N,O-dimethylhydroxylamine hydrochloride (29.1 g, 298 mmol) and pyridine (75 mL, 199 mmol). The mixture was stirred at 25° C. for 16 h. diluted with water (100 mL), and extracted with DCM (4×200 mL). The organic extracts were washed with HCl (1 M, 200 mL) three times, saturated aq. NaHCO$_3$ (200 mL) two times and brine (200 mL), dried over Na$_2$SO$_4$, filtered and concentrated. The residue was purified by silica gel chromatography (PE/EtOAc=15:1 to 3:1) to give F2.

Step 2
To a solution of 2-bromo-1-fluoro-4-methoxybenzene (29.4 g, 143 mmol) in THF (400 mL) was added n-butyllithium (2.5 M in hexane, 57.3 mL, 143 mmol) at −78° C. After 1 h, a solution of F2 (25.0 g, 119 mmol) in THF (50 mL) was added and the reaction mixture was stirred at −78° C. for 2 h. It was quenched with saturated aq. NH$_4$Cl (20 mL), diluted with water (100 mL), and extracted with EtOAc (3×150 mL). The organic extracts were washed with brine (150 mL), dried over Na$_2$SO$_4$, filtered and concentrated. The residue was purified by silica gel chromatography (PE/EtOAc=50:1 to 10:1) to give F3.

Step 3
A mixture of F3 (4 g, 14.58 mmol), (S)-2-methylpropane-2-sulfonamide (2.65 g, 21.87 mmol), and tetraethoxytitanium (6.65 g, 29.2 mmol) in THF (100 mL) was stirred at 50° C. for 3 h and poured into ice-water. The mixture was filtered and the filter cake was washed with ethyl acetate (200 mL). The filtrate was extracted and the organic layer was concentrated. The residue was purified by silica gel chromatography (PE/EtOAc=10:1) to give F4.

Step 4
A solution of n-BuLi (2.5 M in hexane, 2.07 mL, 5.17 mmol) was added to a stirred mixture of 2-methyl-2-(methylsulfonyl)propanenitrile (0.702 g, 4.77 mmol) in THF (16 mL) at −78° C., and the mixture was stirred at −78° C. for 1 h. A solution of F4 (1.5 g, 3.97 mmol) in THF (4 mL) was added to the above mixture. The mixture was stirred at −78° C. for 4 h and quenched with saturated aqueous ammonium chloride (5 mL). It was extracted with ethyl acetate (2×20 mL): the combined organic extracts were washed with brine (2×20 mL), dried over Na$_2$SO$_4$, filtered and the filtrate was concentrated. The residue was purified by silica gel chromatography (PE/EtOAc=1:1) to give F5.

Step 5
A solution of hydrochloric acid (2 mL, 8.0 mmol, 4 N in dioxane) was added to a stirred mixture of F5 (1.7 g, 3.24 mmol) in DCM (10 mL) at 0° C. The mixture was stirred at 25° C. for 2 h, concentrated: the residue was diluted with ethyl acetate (50 mL), aq. NaHCO$_3$ solution (10 mL) and extracted by EtOAc (50 mL). The organic layer was dried over Na$_2$SO$_4$, filtered and the solvent was evaporated under reduced pressure to afford F6, which was used in the next step directly.

Step 6
A mixture of copper(I) chloride (0.659 g, 6.66 mmol) and F6 in EtOH (50 mL) was stirred at 90° C. for 16 h. The mixture was concentrated and the residue was diluted with EtOAc (50 mL) and 20 mL NH$_4$OH (15%). After being stirred for 15 min, the mixture was separated and the organic phase was washed with brine (50 mL), dried over Na$_2$SO$_4$, filtered and concentrated. The residue was purified by silica gel chromatography (PE/EtOAc=1:1) to give F7.

Step 7
Compound F7 (1 g, 2.378 mmol) was separated by SFC (AD-H column) to give F8.

Step 8
A mixture of F8 (15.5 g, 36.9 mmol), di-tert-butyl dicarbonate (12.07 g, 55.3 mmol) and DIEA (12.88 mL, 73.7 mmol) in DCM (120 mL) was stirred at 30° C. for 16 h. The mixture was washed with HCl (1 N aq., 20 mL) and saturated aq. NaHCO$_3$ (20 mL), filtered, dried with Na$_2$SO$_4$ and concentrated. The residue was purified by silica gel chromatography (PE/EtOAc=30:1 to 10:1) to give F9.

Step 9
A solution of LiHMDS (1 M in THF, 19.0 mL, 19.0 mmol) was added to a stirred mixture of F9 (3.0 g, 5.76 mmol) in THF (60 mL) at −40° C., and the mixture was stirred at −40° C. for 1 h. After addition of (R)-2-methyloxirane (0.669 g, 11.5 mmol) at −40° C., the mixture was warmed and stirred at 20° C. for 4 h, and quenched by saturated aqueous ammonium chloride (1 mL). The mixture was extracted with ethyl acetate (2×20 mL); the combined organic extracts were washed with brine (20 mL), dried over Na$_2$SO$_4$, and filtered, and the filtrate was evaporated under reduced pressure. The residue was purified by silica gel chromatography (PE/EtOAc=4:1) to give F10.

Step 10
A mixture of F10 (4.5 g, 7.78 mmol), dihydroxypalladium (1.2 g, 1.709 mmol) (20%) and HCl (4 M in dioxane, 0.5 mL) in MeOH (100 mL) was stirred at 40° C. for 18 h under H$_2$ atmosphere. The mixture was filtered, and the filter cake was washed with methanol (200 mL). The filtrate was concentrated to give crude F11, which was used in next step directly.

Step 11
A mixture of F11 (1.5 g, 3.86 mmol) and concentrated HCl (100 mL) was stirred at 110° C. for 48 h and concentrated. Aqueous sodium hydrogen carbonate (saturated, 5 mL) was added and the mixture was evaporated under reduced pressure to give a mixture of F12a and F12b, which was used without further purification.

Step 12
A mixture of F12a and F12b (3 g, 5.05 mmol) with Boc$_2$O (2.34 mL, 10.1 mmol) and DIPEA (1.76 mL, 10.1 mmol) in MeOH (30 mL) was stirred at 30° C. for 24 h. The mixture was concentrated, the residue was purified by silica gel chromatography (PE/EtOAc=5:1) to give F13 and F14.

Step 13
Bromomethylcyclopropane (148 mg, 1.095 mmol) was added to a stirred mixture of F14 (100 mg, 0.219 mmol) and K$_2$CO$_3$ (91 mg, 0.657 mmol) in DMF (5 mL) at 25° C., and the mixture was stirred at 30° C. for 48 h. Water (5 mL) was added and the mixture was extracted with ethyl acetate (2×50 mL). The combined organic extracts were washed with brine (5×50 mL), dried over Na$_2$SO$_4$, filtered and the solvent was evaporated under reduced pressure. The residue was purified by preparative silica gel TLC eluting with PE/EtOAc=3:1 to give F15 and F16.

Step 14
TFA (0.5 mL, 6.5 mmol) was added to a stirred mixture of F15 (5 mg, 9.8 μmol) in DCM (3 mL) at 0° C., and the mixture was stirred at 20° C. for 2 h. The reaction mixture was concentrated. The residue was purified by p-HPLC to give Example 8.

Example 9 was prepared from intermediate F16 using step 14.

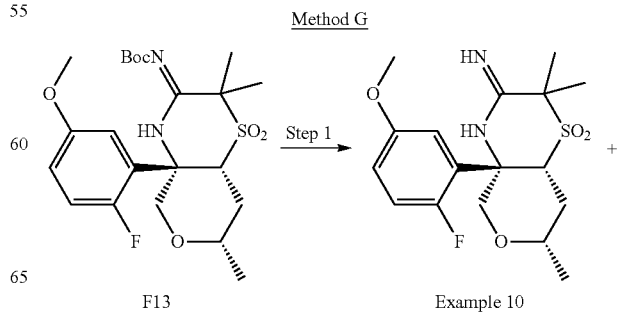

Method G

-continued

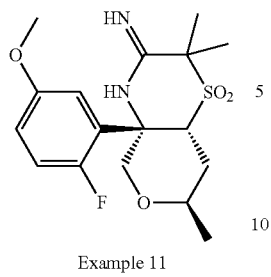

Example 11

Step 1

TFA (0.5 mL, 6.49 mmol) was added to a stirred mixture of F13 (20 mg, 0.043 mmol) in DCM (3 mL) at 0° C., and the mixture was stirred at 20° C. for 1 h. The reaction mixture was concentrated. The residue was purified by p-HPLC to give Example 10 and Example 11.

Method H

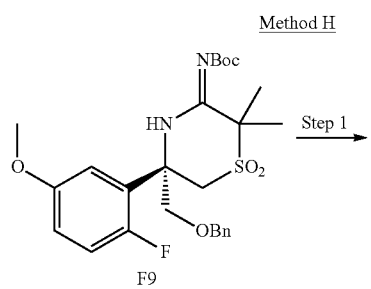

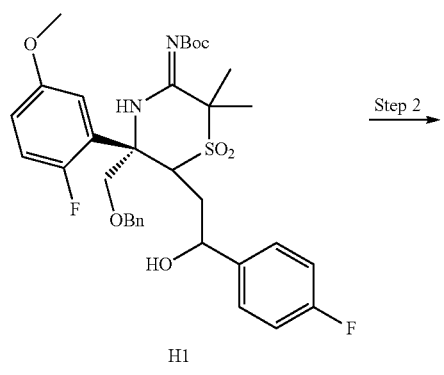

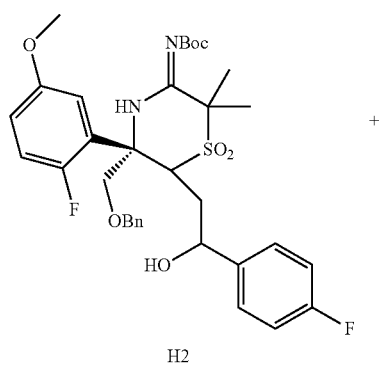

-continued

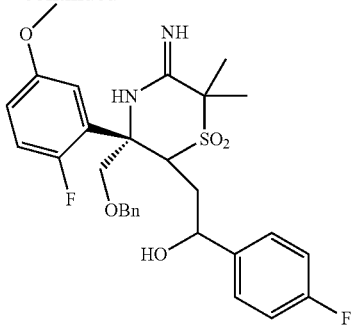

H3

Step 1

A solution of lithium bis(trimethylsilyl)amide (1 M in THF, 7.68 mL, 7.68 mmol) was added to a stirred mixture of compound F9 (1 g, 1.921 mmol) in THF (3 mL) at −40° C., and the mixture was stirred at −40° C. for 1 h. To the mixture was added 2-(4-fluorophenyl)oxirane (0.531 g, 3.84 mmol) at −40° C. The mixture was stirred at 20° C. for 4 h and quenched with aqueous ammonium chloride (saturated, 1 mL), extracted with ethyl acacate (2×20 mL). The combined organic extracts were washed with brine (saturated, 20 mL), dried over $Na_2SO_4$, filtered and the filtrate was evaporated under reduced pressure. The residue was purified by silica gel chromatography (PE/EtOAc=1:1) to give H1.

Step 2

To a solution of H1 (650 mg, 0.99 mmol) in MeOH (8 mL) were added dihydroxypalladium (80 mg, 0.114 mmol, 20%) and HCl (4 M in dioxane, 0.4 mL, 4.80 mmol). The mixture was stirred at 15° C. under $H_2$ atmosphere (15 psi) for 4 h. Then it was filtered through celite to remove $Pd(OH)_2$ and the filtrate was concentrated to give a mixture of H2 and H3.

Medthod I

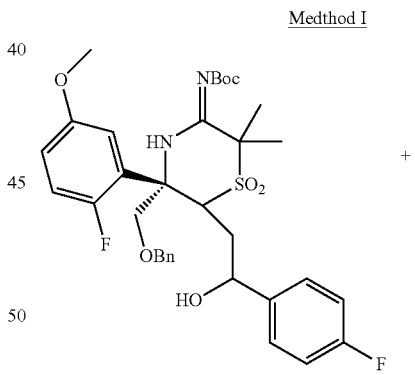

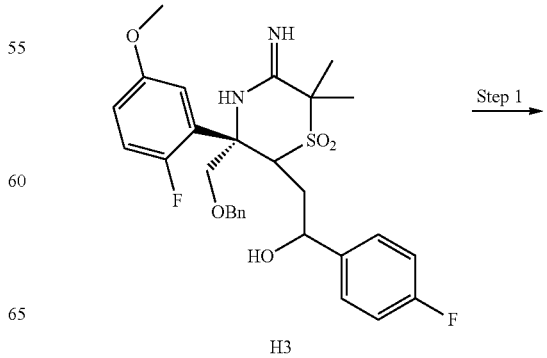

53

-continued

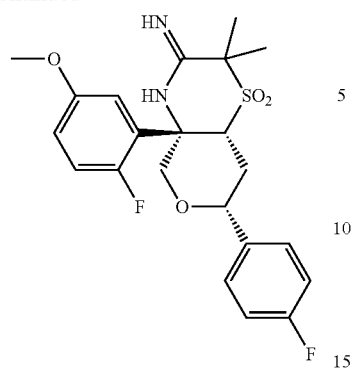

Example 12

Step 1

To a solution of a mixture of H2 and H3 (300 mg, 0.528 mmol) in acetonitrile (10 mL) was added boron trifluoride diethyl etherate (3.32 mL, 13.19 mmol) at 40° C. The mixture was stirred at 40° C. for 16 h and cooled to 15° C. It was diluted with saturated aq. NaHCO$_3$ (50 mL) and extracted with EtOAc (3×120 mL). The combined organic extracts were washed with brine (2×50 mL), dried over Na$_2$SO$_4$, filtered and concentrated. The residue was purified by p-HPLC to give Example 12.

Method J

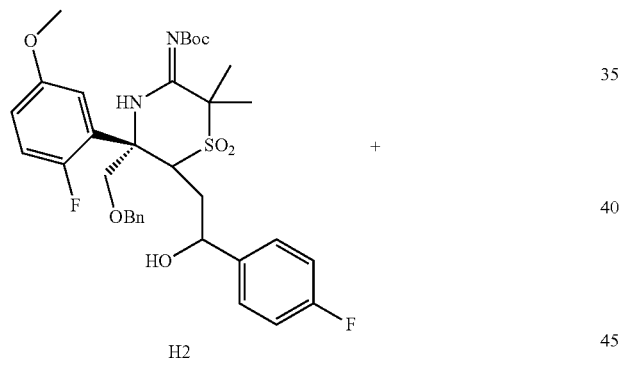

H2

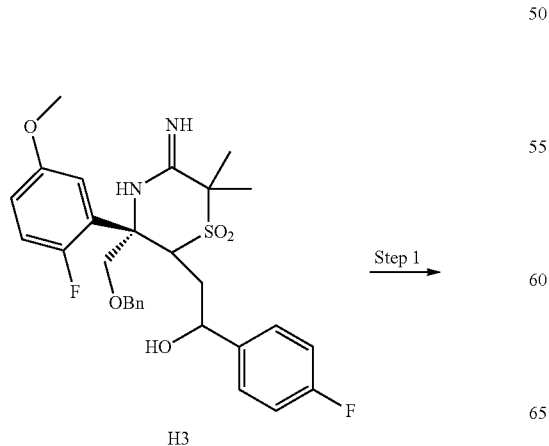

H3

54

-continued

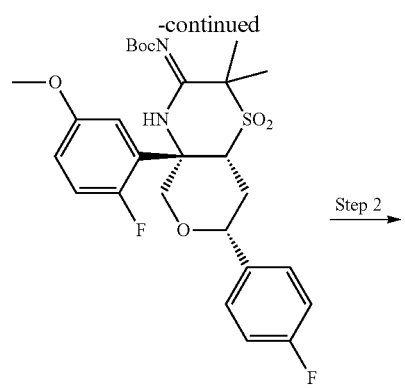

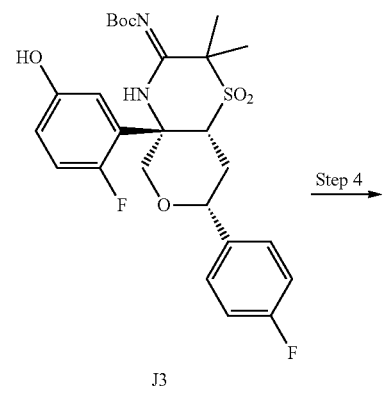

J2

J3

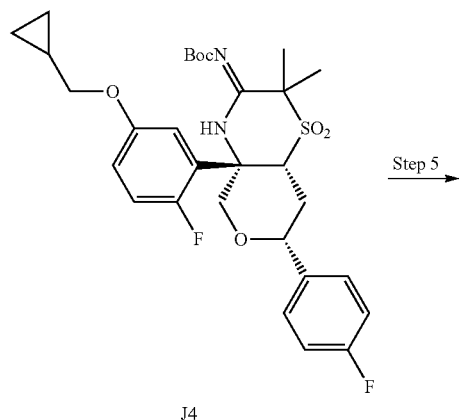

J4

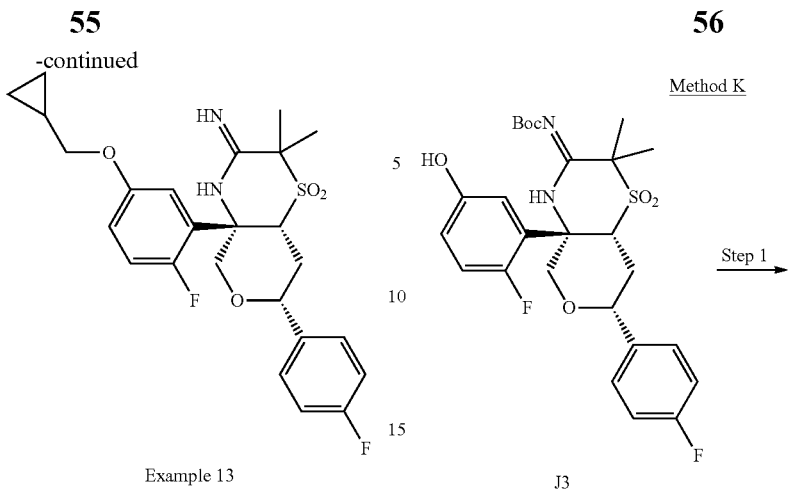

Example 13

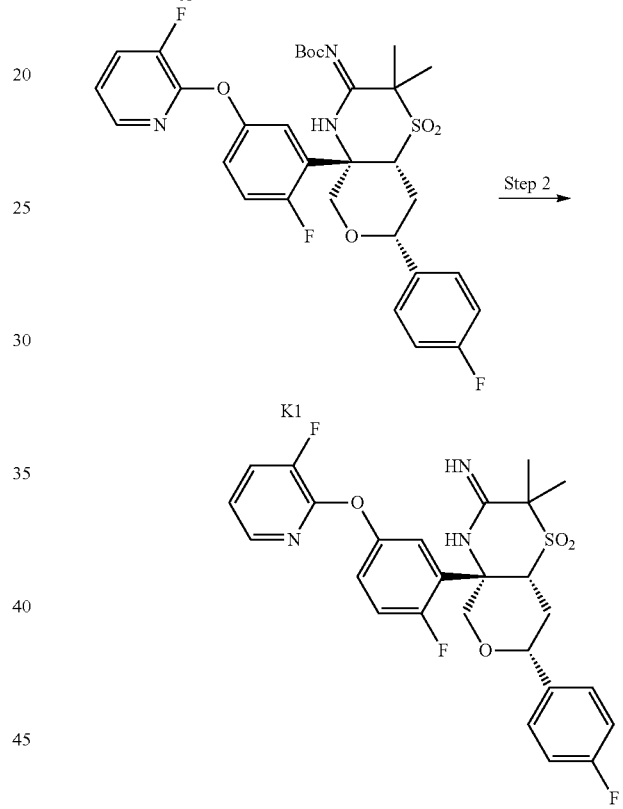

Method K

Example 14

Step 1

To a solution of a mixture of H2 and 113 (1.0 g, 1.76 mmol) with Ph₃P (1.384 g, 5.28 mmol) in DCM (10 mL) was added DIAD (1.03 mL, 5.28 mmol) at 0° C. The mixture was stirred at 18° C. for 4 h and concentrated. The residue was purified by silica gel chromatography (PE/EtOAc=7:1) to give J1.

Step 2

A mixture of J1 (80 mg, 0.178 mmol) and pyridine hydrochloride (103 mg, 0.89 mmol) in a sealed tube was stirred at 180° C. for 6 h and cooled to RT. The mixture was diluted with water (50 mL) and extracted with EtOAc (2×35 mL). The organic extracts were washed with brine (10 mL), dried over Na₂SO₄, filtered and concentrated to afford J2, which was used in the next step without further purification.

Step 3

A solution of J2 (80 mg, 0.183 mmol), DIEA (0.096 mL, 0.550 mmol) and di-tert-butyl dicarbonate (60.0 mg, 0.275 mmol) in CH₂Cl₂ (2 mL) was stirred at 15° C. for 5 h. The mixture was concentrated and the residue was purified by p-TLC (PE: EtOAc=2:1) to afford J3.

Step 4

A mixture of J3 (50 mg, 0.093 mmol), bromomethylcyclopropane (12.58 mg, 0.093 mmol) and K₂CO₃ (38.6 mg, 0.28 mmol) in DMF (0.5 mL) was stirred at 45° C. for 6 h. The mixture was diluted with water (30 mL) and extracted with EtOAc (3×25 mL). The organic extracts were dried over Na₂SO₄ and filtered to afford crude J4, which was used in the next step without further purification.

Step 5

To a solution of J4 (70 mg, 0.12 mmol) in DCM (2.5 mL) was added TFA (0.5 mL, 6.5 mmol). The mixture was stirred at 15° C. for 1 h and concentrated; the residue was purified by p-HPLC to afford Example 13.

Step 1

A mixture of J3 (30 mg, 0.056 mmol), 2,3-difluoropyridine (19.30 mg, 0.168 mmol) and Cs₂CO₃ (54.6 mg, 0.168 mmol) in DMSO (0.5 mL) was stirred at 65° C. for 2 h. It was diluted with water (30 mL) and extracted with EtOAc (3×25 mL). The organic extracts were dried over Na₂SO₄ and filtered to afford K1, which was used in the next step without further purification.

Step 2

To a solution of K1 (32 mg, 0.051 mmol) in DCM (2.5 mL) was added TFA (0.5 mL, 6.5 mmol). The mixture was stirred at 15° C. for 2.5 h and concentrated; the residue was purified by p-HPLC to afford Example 14.

Example 15 was prepared from intermediate J3 similarly by replacing 2,3-difluoropyridine with the appropriate reagent in step 1.

Example 15

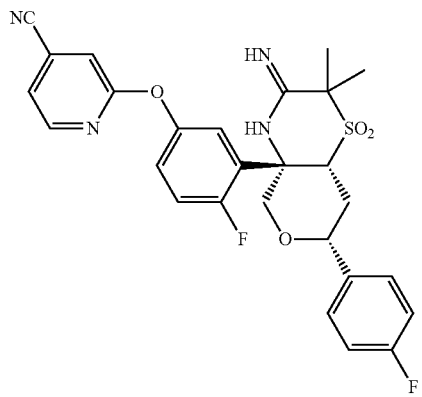 [SMILES: CC1(C)C(=N)N[C@@]2(c3cc(Oc4cc(C#N)ccn4)ccc3F)CO[C@@H](c3ccc(F)cc3)C[C@H]2S1(=O)=O]

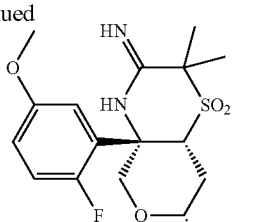

Example 16

Step 1

To a stirred mixture of F9 (2 g, 3.84 mmol) in THF (30 mL) at −40° C. was added lithium bis(trimethylsilyl)amide (1 M in THF, 13.45 mL, 13.45 mmol). After stirring at −40° C. for 1 h, to the solution was added 2-(methoxymethyl)oxirane (0.677 g, 7.68 mmol). The mixture was stirred at 20° C. for 3 h, quenched by aqueous ammonium chloride (saturated, 20 mL) and extracted with ethyl acetate (3×30 mL). The combined organic extracts were washed with brine (20 mL), dried over Na₂SO₄, filtered and concentrated. The residue was purified by silica gel column (PE/EtOAc=10:1 to 1:1) to give L1.

Step 2

A mixture of L1 (1.7 g, 2.79 mmol) and Pd(OH)₂ (20%, 300 mg, 0.427 mmol) in MeOH (50 mL) was stirred at 30° C. under H₂ atmosphere (50 psi) for 24 h. The mixture was filtered and the filtrate was concentrated to give L2.

Step 3

A mixture of 4-methylbenzenesulfonic acid hydrate (3.49 g, 18.35 mmol) and L2 (1.28 g, 3.06 mmol) in toluene (15 mL) was stirred at 130° C. for 35 h and concentrated. The residue was diluted with H₂O (100 mL) and extracted with DCM/isopropanol (3:1; 3×80 mL). The organic extracts were washed with saturated aq. NaHCO₃ (3×50 mL), brine (50 mL), dried over Na₂SO₄, filtered. The filtrate was concentrated to give crude L3 (400 mg).

Step 4

Compound L3 was separated by p-HPLC to give crude Example 16, which was further subjected to SFC (AD column, 250 mm×30 mm, 5 um), then to p-HPLC to give Example 16.

Method L

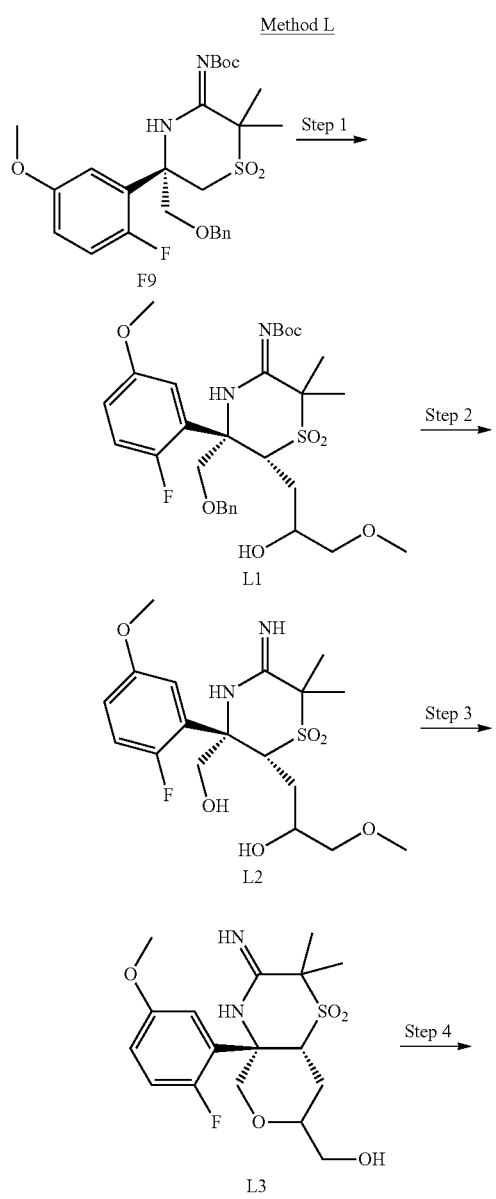

Method M

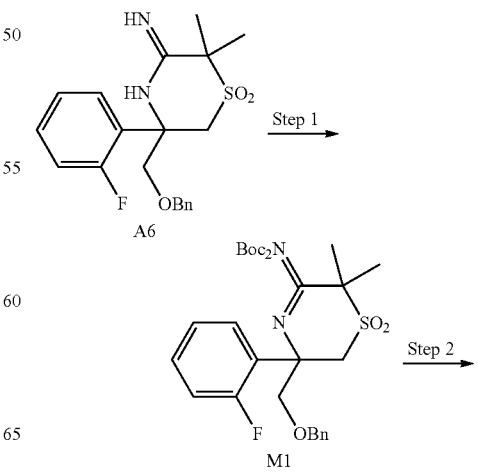

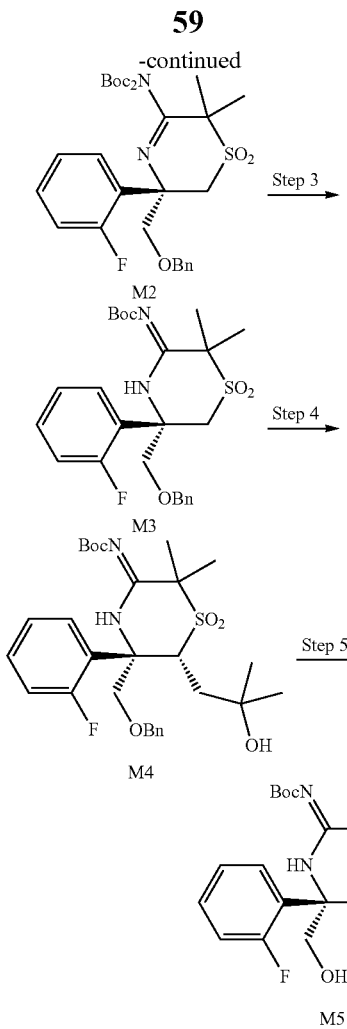

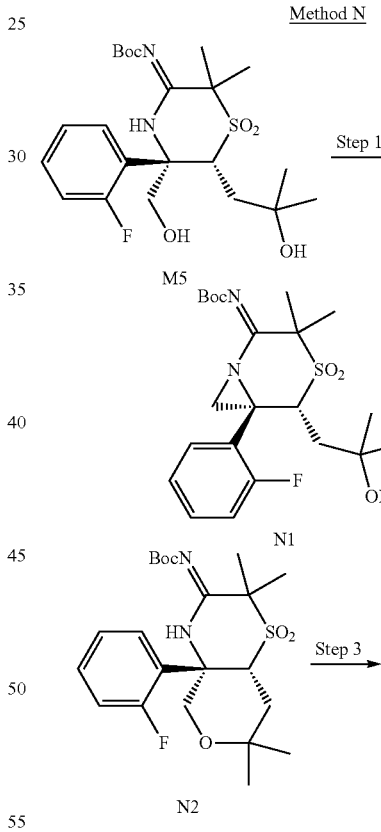

Step 1

To a solution of A6 (7.0 g, 18 mmol) in DCM (100 mL) was added Boc$_2$O (9.7 g, 45 mmol), DIEA (4.6 g, 36 mmol) and DMAP (2.2 g, 18 mmol). The mixture was stirred at 30° C. for 16 h, then concentrated and purified by silica gel chromatography (PE:EA=20:1) to afford M1.

Step 2

M1 (4.9 g, 8.31 mmol) was dissolved in dichloromethane (49 mL). The mixture of enantiomers were separated using SFC (IC column, 5×25 cm, 5 um) to give M2.

Step 3

To a stirred solution of M2 (2.0 g, 3.39 mmol) in DCM (16.9 mL) was added trifluoroacetic acid (1.30 mL, 16.9 mmol). The reaction was allowed to stir for 15 h at room temperature. To the reaction solution was added EtOAc and aqueous saturated sodium bicarbonate. The aqueous layer was extracted with EtOAc (3×) and the combined organic layers were dried with magnesium sulfate, filtered, and concentrated under reduced pressure. The residue was diluted with dichloromethane (16.9 mL) and to the solution was added boc-anhydride (776 mg, 3.56 mmol) followed by triethylamine (1.41 mL, 10.2 mmol). The reaction solution was stirred at room temperature for 15 h. Water was added and the aqueous layer extracted with EtOAc (3×). The combined organic layers were dried with magnesium sulfate, filtered and concentrated under reduced pressure. The residue was purified via silica gel chromatography (hexanes: EtOAc 100:0 to 70:30) to afford M3.

Step 4

To a solution of M3 (1.53 g, 3.11 mmol) in THF (15.6 mL) was added LiHMDS (IM in THF, 7.78 mL, 7.78 mmol) at −20° C. After stirring for 30 min at −20° C., 2,2-dimethyloxirane (0.42 mL, 4.67 mmol) was added. The reaction was taken out of the cooling bath and allowed to warm to room temperature over 4 h. The reaction was quenched with aqueous saturated ammonium chloride. The aqueous layer was extracted with EtOAc (3×). The combined organic layers were dried with magnesium sulfate, filtered, and concentrated under reduced pressure. The residue was purified by silica gel chromatography (hexane:EtOAc 100:0 to 50:50) to afford M4.

Step 5

To a mixture of M4 (1.47 g, 2.62 mmol) in MeOH (40 mL) was added palladium hydroxide (1.84 g, 2.62 mmol). The reaction mixture was run on the Parr shaker at 50 psi for 15 h at room temperature. The reaction was filtered through a celite pad, washing with MeOH. The organic layer was concentrated under reduced pressure and the residue purified by silica gel chromatography (hexane:EtOAc 100:0 to 50:50) to afford M5.

Step 1

To a mixture of MS (795 mg, 1.68 mmol) and triphenylphosphine (620 mg, 2.37 mmol) in DCM (32 mL) was added DIAD (0.46 mL. 2.37 mmol) at 0° C. The reaction was allowed to warm to room temperature with the ice bath over a 15 h period. Water was added, and the phases were separated and the aqueous layer extracted with EtOAc (3×). The combined organic layers were dried with magnesium sulfate, filtered and concentrated under reduced pressure. The residue was purified by silica gel chromatogrpahy (hexane:[3:1 EtOAc/EtOH] 100:0 to 80:20) to afford N1.

Step 2

Acetonitrile (13 mL) was added to a sealed tube containing N1 (606 mg, 1.58 mmol). The reaction mixture was cooled to −10° C., and methanesulfonic acid (0.51 mL, 7.81 mmol) was added. The reaction was stirred for 10 min, and then 1,3-dibromo-5,5-dimethylimidazolidine-2,4-dione (372 mg, 1.30 mmol) was added. The reaction was taken out of the cooling bath and heated at 50° C. for 3 h. Additional 1,3-dibromo-5,5-dimethylimidazolidine-2,4-dione (186 mg, 0.65 mmol) was then added, and the mixture was then stirred at 50° C. for 4 h and then at room temperature for 15 h. The reaction was quenched with aqueous saturated sodium bicarbonate and extracted with EtOAc (3×). The combined organic layers were dried with magnesium sulfate, filtered and concentrated under reduced pressure. To the residue was added DCM (15 mL) followed by triethylamine (0.55 mL, 3.91 mmol) and Boc-anhydride (313 mg, 1.43 mmol). The reaction was stirred at room temperature for 4 h. Water was added and the aqueous layer extracted with EtOAc (3×). The combined organic layers were dried with magnesium sulfate, filtered and concentrated. The residue was purified by silica gel chromatography (hexane:EtOAc 100:0 to 80:20) to afford N2.

Step 3

To a solution of N2 (18 mg, 0.04 mmol) in DCM (1 mL) was added trifluoroacetic acid (0.03 mL. 0.396 mmol). The reaction was stirred at room temperature for 15 h. The reaction was quenched with aqueous saturated sodium bicarbonate and extracted 3× with DCM. The combined organic layers were dried with magnesium sulfate, filtered and concentrated. The residue was purified via silica gel chromatography (hexanes: [3:1 EtOAc:EtOH with 2% NH$_4$OH] 100:0 to 50:50) to afford Example 17.

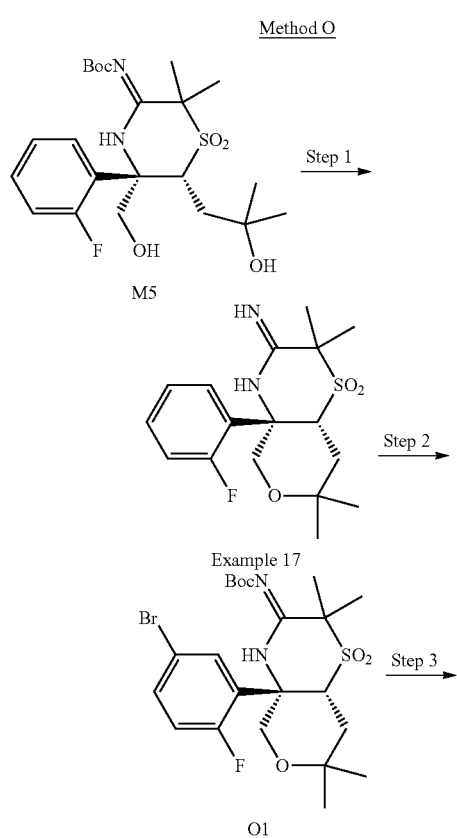

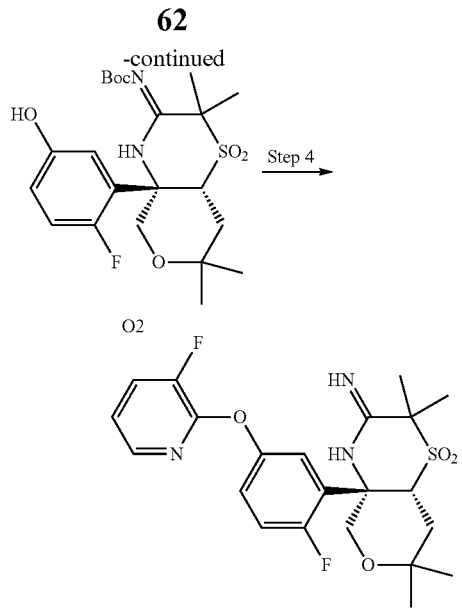

Example 18

Step 1

A solution of M5 (1.36 g, 2.88 mmol) in concentrated HCl (30 mL) was heated to 110° C. for 2 h. The reaction was cooled to room temperature and quenched with ammonium hydroxide. The aqueous layer was extracted with EtOAc (3×). The combined organic layers were dried with magnesium sulfate, filtered, and concentrated under reduced pressure. The residue was purified by silica gel chromatography (hexane:[3:1 EtOAc:EtOH with 2% NH$_4$OH], 100:0 to 50:50) to afford Example 17.

Step 2

To a solution of Example 17 (1.12 g, 3.16 mmol) in acetonitrile (32 mL) was added sulfuric acid (1.01 mL, 19.0 mmol) at −10° C. The reaction was stirred for 10 min and then 1,3-dibromo-5,5-dimethylimidazolidine-2,4-dione (542 mg, 1.90 mmol) was added. The reaction was heated to 50° C. for 16 h. The reaction was quenched with saturated aq. sodium bicarbonate and extracted with EtOAc (3×). The combined organic layers were dried with magnesium sulfate, filtered, and concentrated under reduced pressure. To the residue was added DCM (15 mL) followed by triethylamine (1.32 mL, 9.48 mmol) and Boc-anhydride (966 mg, 4.42 mmol). The reaction was stirred for 4 h at room temperature. Water was added and the aqueous layer was separated and extracted with EtOAc (3×). The combined organic layers were dried with magnesium sulfate, filtered, and concentrated. The residue was purified by silica gel chromatography to afford O1.

Step 3

To a solution of 01 (751 mg, 1.41 mmol) in DMSO (10 mL) was added phosphazene base β$_2$-Et (1.41 mL, 4.22 mmol), Di-Ad-BrettPhos-G3-Palladacycle (142 mg, 0.14 mmol), and water (0.13 mL, 7.0 mmol). The reaction solution was sealed and purged with nitrogen gas via subsurface bubbling. The reaction was heated to 40° C. for 4 h. The reaction was diluted with EtOAc and washed with water (3×). The organic layer was dried with magnesium sulfate, filtered, and concentrated under reduced pressure. The residue was purified by silica gel chromatography (hexane:EtOAc 100:0 to 50:50) to afford 02.

Step 4

To a solution of 02 (75 mg, 0.16 mmol) in DMSO (2 mL) were added 2,3-difluoropyridine (0.02 mL, 0.24 mmol) and cesium carbonate (104 mg, 0.32 mmol). The reaction was heated to 70° C. for 1 h. It was diluted with EtOAc and washed with water (3×). The organic layer was dried with magnesium sulfate, filtered, and concentrated under reduced pressure. To the residue was added DCM (2 mL) followed by trifluoroacetic acid (0.37 mL, 4.78 mmol). The reaction was stirred for 4 h at room temperature. The reaction was quenched with aqueous saturated sodium bicarbonate and extracted with EtOAc (3×). The combined organic layers were dried with magnesium sulfate, filtered, and concentrated under reduced pressure. The residue was purified by silica gel chromatography (hexane:[3:1 EtOAc:EtOH], 100:0 to 60:40) to afford Example 18.

Examples 19, 20 and 21 were prepared similarly from intermediate 02 replacing 2,3-difluoropyridine with the appropriate reagent in Step 4 above.

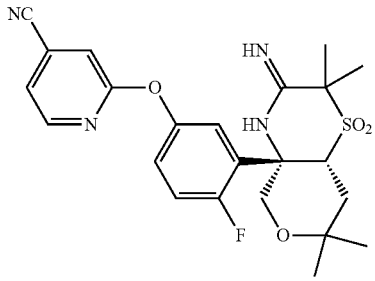 [SMILES: CC1(C)C[C@@H]2[C@](c3cc(Oc4cc(C#N)ccn4)ccc3F)(CO1)NC(=N)C(C)(C)S2(=O)=O]

Example 19

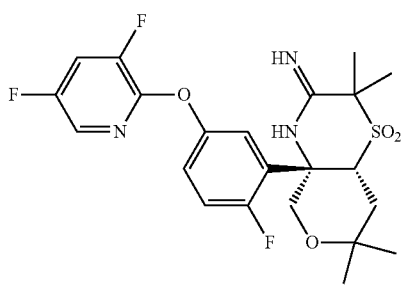 [SMILES: CC1(C)C[C@@H]2[C@](c3cc(Oc4ncc(F)cc4F)ccc3F)(CO1)NC(=N)C(C)(C)S2(=O)=O]

Example 20

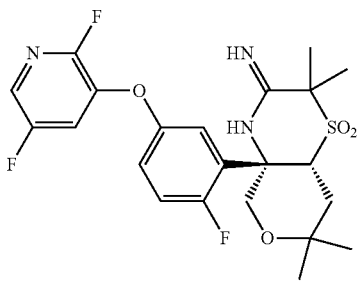 [SMILES: CC1(C)C[C@@H]2[C@](c3cc(Oc4cc(F)cnc4F)ccc3F)(CO1)NC(=N)C(C)(C)S2(=O)=O]

Example 21

Method P

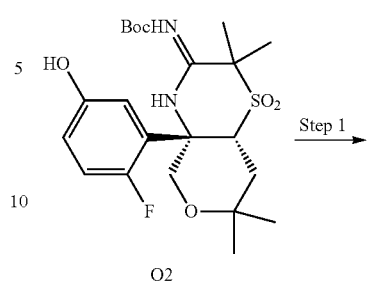

02

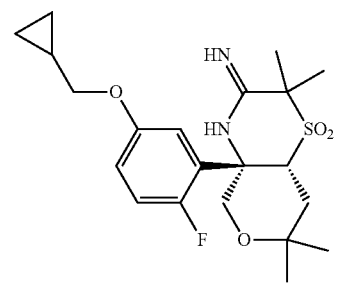 [SMILES: CC1(C)C[C@@H]2[C@](c3cc(OCC4CC4)ccc3F)(CO1)NC(=N)C(C)(C)S2(=O)=O]

Example 22

Step 1

To a solution of 02 (50 mg, 0.11 mmol) in DMSO (1 mL) were added bromomethylcyclopropane (0.012 mL, 0.13 mmol) and potassium carbonate (22 mg, 0.16 mmol). The reaction was stirred at room temperature for 15 h. The reaction was diluted with EtOAc and washed with water (3×). The organic layer was dried with magnesium sulfate, filtered, and concentrated under reduced pressure. The residue was diluted with DCM (2 mL) and trifluoroacetic acid was added. The reaction was stirred at room temperature for 4 h. It was quenched with aqueous saturated sodium bicarbonate and extracted with EtOAc (3×). The combined organic layers were dried with magnesium sulfate, filtered, and concentrated under reduced pressure. The residue was purified via reverse phase chromatography (water:MeCN, 75:25 to 40:60) to afford Example 22.

Example 23 was prepared similarly from intermediate 02 substituting bromomethylcyclopropane with the appropriate reagent.

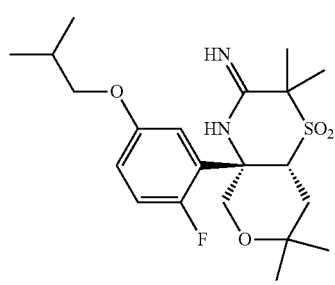

Example 23

Method Q

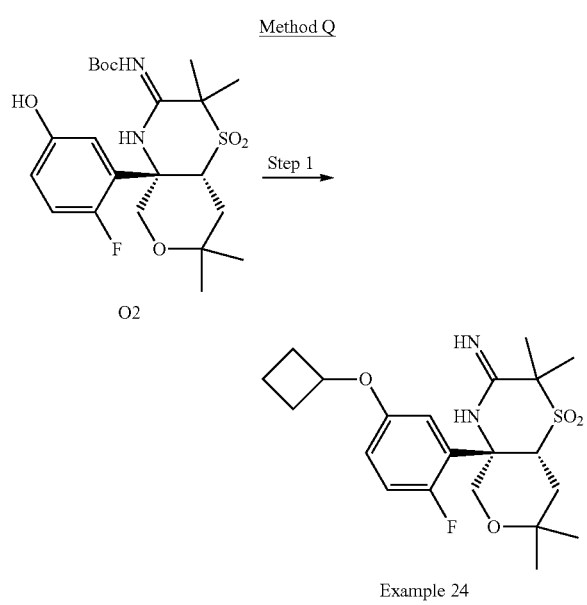

Example 24

Step 1

To a solution of O2 (50 mg, 0.11 mmol) in DMSO (1 mL) were added bromocyclobutane (0.02 mL, 0.16 mmol) and cesium carbonate (69 mg, 0.21 mmol). The reaction was heated to 70° C. for 1 h. It was diluted with EtOAc and washed with water (3×). The organic layer was dried with magnesium sulfate, filtered, and concentrated under reduced pressure. The residue was diluted with DCM (2 mL) and trifluoroacetic acid (0.25 mL, 3.2 mmol) was added. The reaction was stirred at room temperature for 4 h. The reaction was quenched with aqueous saturated sodium bicarbonate and extracted with EtOAc (3×). The combined organic layers were dried with magnesium sulfate, filtered and concentrated under reduced pressure. The residue was purified by silica gel chromatography (hexane:[3:1 EtOAc:EtOH with 2% NH₄OH], 100:0 to 60:40) to afford Example 24.

Method R

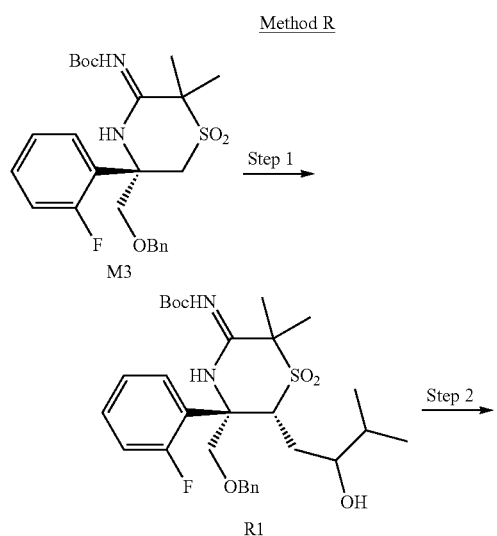

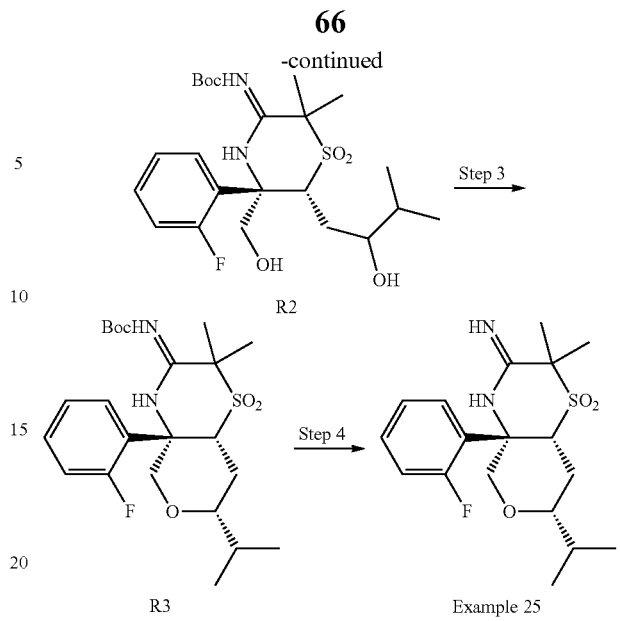

Example 25

Step 1

To a solution of M3 (5.0 g, 10.2 mmol) in THF (51 mL) was added LiHMDS (1M in THF, 25.5 mL, 25.5 mmol) at −20° C. The reaction was stirred for 30 minutes, then 2-isopropyloxirane (1.61 mL, 15.3 mmol) was added. The reaction solution was taken out of the cooling bath and allowed to warm to room temperature over 14 h. The reaction was quenched with aqueous saturated ammonium chloride and extracted with EtOAc (3×). The combined organic layers were dried with magnesium sulfate, filtered, and concentrated under reduced pressure. The residue was purified by silica gel chromatography (hexane:EtOAc 100:0 to 60:40) to afford R1.

Step 2

To a solution of R1 (5.19 g, 9.0 mmol) in MeOH was added 20% palladium hydroxide on carbon (6.32 g, 9.0 mmol). The reaction was run on the Parr shaker at 50 psi for 15 h at room temperature. The reaction was only 50% completed so additional 20% palladium hydroxide on carbon (3.16 g, 4.5 mmol) was added. The reaction was subjected to the Parr shaker at 50 psi for additional 15 h at room temperature. The reaction was filtered through celite, washing with MeOH. The filtrate was concentrated to afford R2.

Step 3

Concentrated HCl (45 mL, 548 mmol) was added to R2 (4.38 g, 9.0 mmol). The reaction was heated at 110° C. for 2 h, cooled to RT and quenched with aqueous NH₄OH. The mixture was extracted with EtOAc (3×). The combined organic layers were dried with magnesium sulfate, filtered, and concentrated under reduced pressure. To the residue was added DCM (90 mL) followed by triethylamine (3.76 mL, 27 mmol) and Boc anhydride (2.36 g 10.8 mmol). The mixture was stirred for 4 h, diluted with water and extracted EtOAc (3×). The combined organic layers were dried with magnesium sulfate, filtered, and concentrated under reduced pressure. The residue was purified by silica gel chromatography (hexane:EtOAc 100:0 to 80:20). The combined fractions were concentrated and the isomers separated by SFC (OD-H 21×250 mm) to afford R3.

Step 4

To a solution of R3 (10 mg, 0.02 mmol) in DCM (1 mL) was added trifluoroacetic acid (0.1 mL, 1.3 mmol). The reaction was stilled at room temperature for 15 h and quenched with aqueous saturated sodium bicarbonate. The aqueous layer was extracted with EtOAc (3×). The combined organic layers were dried with magnesium sulfate, filtered, and concentrated under reduced pressure. The residue was purified by silica gel chromatography (hexane:[3:1 EtOAc:EtOH with 2% NH₄OH], 100:0 to 40:60) to afford Example 25.

Specific non-limiting examples of compounds of the invention are shown in Table 1 below. As noted above, while only one tautomeric form of each compound is shown in the tables, it shall be understood that both tautomeric forms of the compounds are contemplated as being within the scope of the non-limiting examples.

TABLE 1

| Ex | Structure / IUPAC Name / HNMR (where indicated) | LCMS m/z (M + 1) | BACE-1 Ki (nM) | BACE-2 Ki (nM) |
|---|---|---|---|---|
| 1 | [Structure] $\delta$ (400 MHz, CDCl$_3$): 1.31 (3H, d, J = 6.2 Hz), 1.40 (3H, s), 1.79-1.67 (4H, m), 2.22-2.12 (1H, m), 3.72 (1H, dd, J = 5.1, 10.6 Hz), 3.99-3.80 (2H, m), 4.34 (1H, td, J = 4.4, 13.0 Hz), 7.13-6.99 (2H, m), 7.39-7.27 (2H, m). (4aS,7S,8aR)-4a-(2-fluorophenyl)-3-imino-2,2,7-trimethyloctahydropyrano[4,3-b][1,4]thiazine 1,1-dioxide | 341.1 | 362.6 | 72.5 |
| 2 | [Structure] $\delta$ (400 MHz, CDCl$_3$): 1.17 (3H, d, J = 6.2 Hz), 1.52 (1H, ddd, J = 6.2, 12.0, 15.2 Hz), 1.68 (3H, s), 1.84 (3H, s), 2.44 (1H, d, J = 15.2 Hz), 3.88 (1H, d, J = 5.5 Hz), 4.29-4.19 (2H, m), 4.38 (1H, dd, J = 6.0, 9.7 Hz), 7.03 (1H, dd, J = 7.9, 12.6 Hz), 7.21-7.15 (1H, m), 7.33-7.27 (1H, m), 8.01 (1H, t, J = 7.6 Hz). (4aS,7R,8aR)-4a-(2-fluorophenyl)-3-imino-2,2,7-trimethyloctahydropyrano[4,3-b][1,4]thiazine 1,1-dioxide | 341.1 | 50% inh. @10 μM | 6259 |
| 3 | [Structure] $\delta$ (400 MHz, CD$_3$OD): 1.31 (3H, d, J = 6.0 Hz), 1.49 (3H, s), 1.79-1.68 (1H, m), 1.83 (3H, s), 2.26 (1H, d, J = 13.1 Hz), 3.86-3.73 (1H, m), 3.93 (2H, s), 4.60 (1H, d, J = 12.5 Hz), 7.13 (1H, dd, J = 8.8, 12.3 Hz), 7.44 (1H, d, J = 6.0 Hz), 7.57 (1H, d, J = 7.0 Hz). (4aS,7S,8aR)-4a-(5-bromo-2-fluorophenyl)-3-imino-2,2,7 trimethyloctahydropyrano[4,3-b][1,4]thiazine 1,1-dioxide | 419.0 | 1207 | 398.7 |

TABLE 1-continued

| Ex | Structure HNMR (where indicated) IUPAC Name | LCMS m/z (M + 1) | BACE-1 Ki (nM) | BACE-2 Ki (nM) |
|---|---|---|---|---|
| 4 | | 413.2 | 354.5 | 31.6 |

δ (400 MHz, CD₃OD): 1.02 (6 H, d, J = 6.6 Hz), 1.32 (3H, d, J = 6.2 Hz), 1.52 (3H, s), 1.76 (1H, q, J = 12.4 Hz), 1.87 (3H, s), 2.04 (1H, td, J = 6.6, 13.2 Hz), 2.31 (1H, dd, J = 2.4, 13.5 Hz), 3.78-3.66 (2H, m), 3.83 (1H, dd, J = 5.6, 9.6 Hz), 4.07-3.89 (2H, m), 4.75 (1H, d, J = 12.6 Hz), 6.77 (1H, br. s.), 7.02-6.93 (1H, m), 7.12 (1H, dd, J = 9.2, 12.0 Hz).
(4aS,7S,8aR)-4a-(2-fluoro-5-isobutoxyphenyl)-3-imino-2,2,7-trimethyloctahydropyrano[4,3-b][1,4]thiazine 1,1-dioxide

| 5 | | 452.1 | 17.5 | 4.9 |

δ (400 MHz, CD₃OD): 1.33 (3H, d, J = 6.2 Hz), 1.59 (3H, s), 1.83-1.71 (1H, m), 1.87 (3H, s), 2.33 (1H, dd, J = 2.5, 13.3 Hz), 3.87-3.83 (1H, m), 4.02 (2H q, J = 12.8 Hz), 4.82-4.73 (1H, m), 7.19-7.09 (2H, m), 7.33-7.22 (2H, m), 7.68 (1H, t, J = 9.2 Hz), 7.86 (1H, d, J = 4.6 Hz)
(4aS,7S,8aR)-4a-(2-fluoro-543-fluoropyridin-2-yl)oxy)phenyl)-3-imino-2,2,7-trimethyloctahydropyrano[4,3-b][1,4]thiazine 1,1-dioxide

| 6 | | 459.1 | 23.6 | 19.2 |

δ (400 MHz, CD₃OD): 1.32 (3H, d, J = 6.2 Hz), 1.57 (3H, s), 1.82-1.71 (1H, m), 1.86 (3H, s), 2.32 (1H, dd, J = 2.5, 13.3 Hz), 3.84 (1H, dd, J = 6.1, 9.4 Hz), 4.13-3.94 (2H, m), 4.77 (1H, td, J = 3.9, 12.6 Hz), 7.16 (1H, d, J = 4.6 Hz), 7.34-7.22 (2H, m), 7.44-7.36 (2H, m), 8.26 (1H, d, J = 5.1 Hz)
2-(4-fluoro-3-((4aS,7S,8aR)-3-imino-2,2,7-trimethyl-1,1-dioxidooctahydropyrano[4,3-b][1.4]thiazin-4a-yl)phenoxy)isonicotinonitrile

| 7 | | 470.2 | 53.6 | 28.9 |

δ (400 MHz, CD₃OD): 1.32 (3H, d, 3 = 6.0 Hz), 1.56 (3H, s), 1.75 (1H, d, J = 13.0 Hz), 1.86 (3H, s), 2.32 (1H, dd, J = 13.6, 2.5 Hz), 3.84 (1H, dd, J = 9.7, 5.5 Hz), 4.00 (2H, d, J = 8.6 Hz), 4.77 (1H, dt, J = 8.5, 4.1 Hz), 7.13 (1H, d,

TABLE 1-continued

| | | LCMS m/z (M + 1) | BACE-1 Ki (nM) | BACE-2 Ki (nM) |
|---|---|---|---|---|
| | Structure | | | |
| | HNMR (where indicated) | | | |
| Ex | IUPAC Name | | | |

J = 4.4 Hz), 7.20-7.33 (2H, m), 7.68-7.78 (1H, m), 7.83 (1H, d, J = 2.4 Hz)
(4aS,7S,8aR)-4a-(5-((3,5-difluoropyridin-2-yl)oxy)-2-fluorophenyl)-3-imino-
2,2,7-trimethyloctahydropyrano[4,3-b][1,4]thiazine 1,1-dioxide

| 8 | | 411.3 | 4481 | 1181 |

δ (400 MHz, CD$_3$OD): 0.02 (2H, d, J = 5.1 Hz), 0.29 (2H, d, J = 7.1 Hz), 0.86
(3H, d, J = 6.0 Hz), 0.99-0.90 (1H, m), 1.37-1.22 (1H, m), 1.48 (3H, s),
1.61 (3H, s), 2.14 (1H, d, J = 15.7 Hz), 3.50 (2H, d J = 6.6 Hz), 4.10-3.94 (3 H,
m), 4.20 (1H, d, J = 12.3 Hz), 6.75-6.67 (1H, m), 6.85 (1H, dd, J = 9.3,
12.3 Hz), 7.27 (1H, dd, J = 2.8, 6.7 Hz)
(4aS,7R,8aR)-4a-(5-(cyclopropylmethoxy)-2-fluorophenyl)-3-imino-2,2,7-
trimethyloctahydropyrano[4,3-b][1,4]thiazine 1,1-dioxide

| 9 | | 411.3 | 94.2 | 11.4 |

δ (400 MHz, CD$_3$OD): 0.01 (2H, d, J = 4.4 Hz), 0.28 (2H, d, J = 7.7 Hz), 0.91
(1H, br. s.), 1.00 (3H, d, J = 6.2 Hz), 1.20 (3H, s), 1.49-1.37 (1H, m), 1.54
(3H, s), 1.98 (1H, d, J = 13.5 Hz), 3.54-3.42 (3H, m), 3.72-3.57 (2H, m),
4.42 (1H, d, J = 12.8 Hz), 6.45 (1H, br. s.), 6.67-6.61 (1H, m), 6.79 (1H, dd,
J = 9.3, 11.9 Hz).
(4aS,7S,8aR)-4a-(5-(cyclopropylmethoxy)-2-fluorophenyl)-3-imino-2,2,7-
trimethyloctahydropyrano[4,3-b][1,4]thiazine 1,1-dioxide

| 10 | | 371.1 | 681.2 | 249.3 |

δ (400 MHz, CD$_3$OD): 1.32 (3H, d, J = 6.0 Hz), 1.51 (3H, s), 1.82-1.71 (1H,
m), 1.86 (3H, s), 2.31 (1H, d, J = 13.0 Hz), 3.79 (3H, br. s.), 3.86-3.81 (1H,
m), 4.07-3.88 (2H, m), 4.73 (1H, br. s.), 6.76 (1H, br. s.), 6.98 (1H, br. s.),
7.18-7.08 (1H, m)
(4aS,7S,8aR)-4a-(2-fluoro-5-methoxyphenyl)-3-imino-2,2,7-
trimethyloctahydropyrano[4,3-b][1,4]thiazine 1,1-dioxide TABLE 1-continued

| Structure HNMR (where indicated) | LCMS m/z (M + 1) | BACE-1 Ki (nM) | BACE-2 Ki (nM) |
|---|---|---|---|
| Ex | | | |
| IUPAC Name | | | |

Ex 11

371.1    27% Inh. @10 μM    8396

δ (400 MHz, CD$_3$OD): 1.18 (3H, d, J = 6.2 Hz), 1.63-1.60 (1H, m), 1.80 (3H, s), 1.93 (3H, s), 2.46 (1H ,d, J = 15.7 Hz), 3.80 (3H, s), 4.36-4.25 (2H, m), 4.39 (1H, d, J = 5.5 Hz), 4.52 (1H, d, J = 12.1 Hz), 7.07-6.98 (1H, m), 7.18 (1H, dd, J = 9.2, 12.5 Hz), 7.59 (1H, dd, J = 3.1, 6.8 Hz)
(4aS,7R,8aR)-4a-(2-fluoro-5-methoxyphenyl)-3-imino-2,2,7-trimethyloctahydropyrano[4,3-b][1,4]thiazine 1,1-dioxide Ex 12

451.1    183.8    96.3

δ (400 MHz, CDCl$_3$): 1.65 (3H, br. s.), 1.89 (3H, br. s.), 2.02-1.91 (1H, m), 2.61 (1H, d, J = 12.6 Hz), 3.78 (3H, s), 4.06 (1H, d, J = 12.8 Hz), 4.38 (1H, d, J = 12.8 Hz), 4.79-4.60 (2H, m), 6.75 (1H, br. s.), 6.88 (1H, d, J = 8.2 Hz), 7.09 (3H, d, J = 7.1 Hz), 7.36 (2H, br. s.), 8.81 (1H, br. s.), 11.74 (1H, br. s.)
(4aS,7R,8aR)-4a-(2-fluoro-5-methoxyphenyl)-7-(4-fluorophenyl)-3-imino-2,2-dimethyloctahydropyrano[4,3-b][1,4]thiazine 1,1-dioxide Ex 13

491.1    115.2    11.7

δ (400 MHz, CDCl$_3$): 0.34 (2H, d, J = 4.7 Hz), 0.64 (2H, d, J = 7.8 Hz), 1.25 (1H, br. s.), 1.66 (3H, br. s.), 1.88 (3H, s), 1.93 (1H, d, J = 13.3 Hz), 2.61 (1H, d, J = 14.1 Hz), 3.80-3.68 (2H, m), 4.04 (1H, d, J = 12.9 Hz), 4.38 (1H, d, J = 12.9 Hz), 4.79-4.61 (2H, m), 6.82-6.72 (1H, m), 6.86 (1H, d, J = 9.0 Hz,), 7.15-7.01 (3H, m), 7.36 (2H, dd, J = 5.3, 8.0 Hz), 8.44 (1H, br. s.), 11.94 (1H, br. s.).
(4aS,7R,8aR)-4a-(5-(cyclopropylmethoxy)-2-fluorophenyl)-7-(4-fluorophenyl)-3-imino-2,2-dimethyloctahydropyrano[4,3-b][1,4]thiazine 1,1-dioxide TABLE 1-continued

| Ex | Structure HNMR (where indicated) IUPAC Name | LCMS m/z (M + 1) | BACE-1 Ki (nM) | BACE-2 Ki (nM) |
|---|---|---|---|---|
| 14 | | 532.1 | 3.9 | 1.9 |

δ (400 MHz, CDCl₃): 1.63 (3H, br. s.), 1.84 (3H, s), 1.98-1.86 (1H, m), 2.61 (1H, d, J = 13.5 Hz), 4.08 (1H, d, J = 13.2 Hz), 4.45 (1H, d, J = 12.8 Hz), 4.76-4.63 (2H, m), 7.03-6.96 (1H, m), 7.08 (3H, q, J = 8.5 Hz), 7.23-7.14 (2H, m), 7.40-7.30 (2H, m), 7.46 (1H, t, J = 8.8 Hz), 7.84 (1H, d, J = 4.6 Hz).
(4aS,7R,8aR)-4a-(2-fluoro-5-((3-fluoropyridin-2-yl)oxy)phenyl)-7-(4-fluorophenyl)-3-imino-2,2-dimethyloctahydropyrano[4,3-b][1,4]thiazine 1,1-dioxide

| 15 | | 539.0 | 17.9 | 19.8 |

δ (400 MHz, CDCl₃): 1.62 (3H, s), 1.84 (3H, s), 2.01 (1H, s), 2.62 (1H, d, J = 9.5 Hz), 4.09 (1H, d, J = 12.6 Hz,), 4.43 (1H, d, J = 12.8 Hz,), 4.77-4.62 (2H, m), 7.04-6.99 (1H, m), 7.08 (2H, t, J = 8.6 Hz), 7.25-7.18 (4H, m), 7.35 (2H, dd, J = 5.3, 8.6 Hz), 8.24 (1H, d, J = 5.1 Hz),
2-(4-fluoro-3-((4aS,7R,8aR)-7-(4-fluorophenyl)-3-imino-2,2-dimethyl-1,1-dioxidooctahydropyrano[4,3-b][1,4]thiazin-4a-yl)phenoxy)isonicotinonitrile

| 16 | | 387.1 | 2861 | 2020 |

δ (400 MHz, CD₃OD): 1.39 (3H, s), 1.71 (3H, s), 1.90-1.75 (1H, m), 2.11 (1H, dd, J = 2.9, 13.0 Hz), 3.68-3.57 (3H, m), 3.73 (3H, s), 3.77 (1H, d, J = 11.5 Hz), 3.95-3.87 (1H, m), 4.29 (1H, td, J = 4.2, 13.1 Hz), 6.82 (2H, d d, J = 2.4, 6.4 Hz), 7.04-6.93 (1H, m)
(4aS,7R,8aR)-4a-(2-fluoro-5-methoxyphenyl)-7-(hydroxymethyl)-3-imino-2,2-dimethyloctahydropyrano[4,3-b][1,4]thiazine 1,1-dioxide TABLE 1-continued

| Ex | Structure / IUPAC Name | LCMS m/z (M + 1) HNMR (where indicated) | BACE-1 Ki (nM) | BACE-2 Ki (nM) |
|---|---|---|---|---|
| 17 | (4aS,8aR)-4a-(2-fluorophenyl)-2,2,7,7-tetramethyltetrahydro-2H,5H-pyrano[4,3-b][1.4]thiazin-3(4H)-imine 1,1-dioxide | 355.0 | 299.9 | 293.4 |
| 18 | (4aS,8aR)-4a-{2-fluoro-5-[(3-fluoropyridin-2-yl)oxy]phenyl}-2,2,7,7-tetramethyltetrahydro-2H,5H-pyrano[4,3-b][1,4]thiazin-3(4H)-imine 1,1-dioxide | 466 | 22.4 | 42.2 |
| 19 | (2-{4-fluoro-3-[(4aS,8aR)-3-imino-2,2,7,7-tetramethyl-1,1-dioxidotetrahydro-2H,5H-pyrano[4,3-b][1,4]thiazin-4a(7H)-yl]phenoxy}pyridine-4-carbonitrile | 473 | 33.8 | 65.2 |
| 20 | (4aS,8aR)-4a-{5-[(3,5-difluoropyridin-2-yl)]-2-fluorophenyl}-2,2,7,7-tetramethyltetrahydro-2H,5H-pyrano[4,3-b][1,4]thiazin-3(4H)-imine 1,1-dioxide | 484 | 53.2 | 102.1 |

TABLE 1-continued

| Ex | Structure / IUPAC Name | LCMS m/z (M + 1) HNMR (where indicated) | BACE-1 Ki (nM) | BACE-2 Ki (nM) |
|---|---|---|---|---|
| 21 | (4aS,8aR)-4a-{5-[(2,5-difluoropyridin-3-yl)oxy-2-fluorophenyl}-2,2,7,7-tetramethyltetrahydro-2H,5H-pyrano[4,3-b][1,4]thiazin-3(4H)-imine 1,1-dioxide | 484 | 9.7 | 88.0 |
| 22 | (4aS,8aR)-4a-[5-(cyclopropylmethoxy)-2-fluorophenyl]-2,2,7,7-tetramethyltetrahydro-2H,5H-pyrano[4,3-b][1,4]thiazin-3(4H)-imine 1,1-dioxide | 425 | 120.1 | 35.6 |
| 23 | (4aS,8aR)-4a-[2-fluoro-5-(2-methylpropoxy)phenyl]-2,2,7,7-tetramethyltetrahydro-2H,5H-pyrano[4,3-b][1,4]thiazin-3(4H)-imine 1,1-dioxide | 427 | 172.2 | 66.7 |
| 24 | (4aS,7S,8aR)-4a-(2-fluoro-5-isobutoxyphenyl)-3-imino-2,2,7-trimethyloctahydropyrano[4,3-b][1,4]thiazine 1,1-dioxide | 425 | 182.7 | 108.9 |

TABLE 1-continued

| Ex | Structure HNMR (where indicated) IUPAC Name | LCMS m/z (M + 1) | BACE-1 Ki (nM) | BACE-2 Ki (nM) |
|---|---|---|---|---|
| 25 | ![structure] (4aS,7R,8aR)-4a-(2-fluorophenyl)-2,2-dimethyl-7-(propan-2-yl)tetrahydro-2H,5H-pyrano[4,3-b][1,4]thiazin-3(4H)-imine 1,1-dioxide | 369 | 184.8 | 194.7 |

Assays

Protocols used to determine the recited potency values for the compounds of the invention are described below.

BACE1 HTRF FRET Assay

Reagents:

$Na^+$-Acetate pH 5.0; 1% Brij-35; Glycerol; Dimethyl Sulfoxide (DMSO): Recombinant human soluble BACE1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine $IC_{50}$ values for inhibitors of the soluble human BACE1 catalytic domain. This assay monitors the increase of 620 nm fluorescence that resulted from BACE1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE1 enzyme. Inhibition of BACE1 cleavage of the QSY7-APP$^{swe}$-Eu substrate by inhibitors is manifested as a suppression of 620 nm fluorescence.

Varying concentrations of inhibitors at 3× the final desired concentration in a volume of 10 ul are preincubated with purified human BACE1 catalytic domain (3 nM in 10 µl) for 30 minutes at 30° C., in reaction buffer containing 20 mM Na-Acetate pH 5.0, 10% glycerol, 0.1% Brij-35 and 7.5% DSMO. Reactions are initiated by addition of 10 µl of 600 nM QSY7-APP$^{swe}$-Eu substrate (200 nM final) to give a final reaction volume of 30 µl in a 384 well Nunc HTRF plate. The reactions are incubated at 30° C. for 1.5 hours. The 620 nm fluorescence is then read on a Rubystar HTRF plate reader (BMG Labtechnologies) using a 50 millisecond delay followed by a 400 millisecond acquisition time window. Inhibitor $IC_{50}$ values are derived from non-linear regression analysis of concentration response curves. $K_i$ values are then calculated from $IC_{50}$ values using the Cheng-Prusoff equation using a previously determined µm value of 8 µM for the QSY7-APP$^{swe}$-Eu substrate at BACE1. Observed $K_i$ values for the non-limiting examples are reported in the tables above.

BACE-2 Assay

Inhibitor $IC_{50s}$ at purified human autoBACE-2 are determined in a time-resolved endpoint proteolysis assay that measures hydrolysis of the QSY7-EISEV NLDAEFC-Eu-amide FRET peptide substrate (BACE-HTRF assay). BACE-mediated hydrolysis of this peptide results in an increase in relative fluorescence (RFU) at 620 nm after excitation with 320 nm light. Inhibitor compounds, prepared at 3× the desired final concentration in 1×BACE assay buffer (20 mM sodium acetate pH 5.0, 10% glycerol, 0.1% Brij-35) supplemented with 7.5% DMSO are preincubated with an equal volume of autoBACE-2 enzyme diluted in 1×BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration. $K_m$=8 µM for 4 µM for autoBACE-2) prepared in 1×BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 µs delay on a RUBYstar HTRF plate reader (BMG Labtechnologies). Raw RFU data is normalized to maximum (1.0 nM BACE/DMSO) and minimum (no enzyme/DMSO) RFU values. $IC_{50s}$ are determined by nonlinear regression analysis (sigmoidal dose response, variable slope) of percent inhibition data with minimum and maximum values set to 0 and 100 percent respectively. Similar $IC_{50s}$ are obtained when using raw RFU data. The $K_i$ values are calculated from the $IC_{50}$ using the Cheng-Prusoff equation.

What is claimed is:

1. A compound, or a pharmaceutically acceptable salt thereof, said compound having the structural Formula (I):

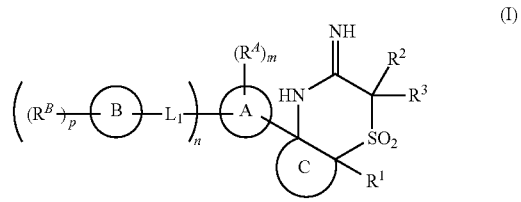

(I)

or a tautomer thereof having the structural Formula (I'):

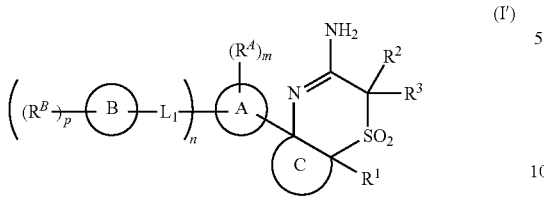

or pharmaceutically acceptable salt thereof, wherein:
ring C is selected from the group consisting of tetrahydrofuranyl and tetrahydropyranyl, wherein 1 or 2 of the ring carbon atoms having two available substitutable hydrogen atoms of said tetrahydrofuranyl and tetrahydropyranyl rings are optionally independently replaced with a —C($R^{C1}R^{C2}$)— group,
wherein $R^{C1}$ and $R^{C2}$ are each independently selected from the group consisting of H, halogen, —$CO_2$—($C_1$-$C_6$-alkyl), alkyl, cycloalkyl, -alkyl-cycloalkyl, heterocycloalkyl, -alkyl-heterocycloalkyl, aryl, -alkyl-aryl, heteroaryl, and -alkyl-heteroaryl,
wherein each said alkyl, cycloalkyl, heterocycloalkyl, aryl, and heteroaryl of $R^{C1}$ and $R^{C2}$ are optionally substituted with one or more $R^3$, and
wherein 1 to 2 non-adjacent, non-terminal carbon atoms in each said alkyl of $R^{C1}$ and $R^{C2}$ are optionally independently replaced with —O—, —NH—, —N($C_1$-$C_6$-alkyl)-, —S—, —S(O)—, or —S(O)$_2$—,
or, alternatively, wherein said $R^{C1}$ and $R^{C2}$ of one said —C($R^{C1}R^{C2}$)— group are taken together with the carbon to which they are attached form a spirocyclic ring consisting of from 3 to 6 carbon atoms,
wherein 1 of said carbon atoms may be replaced with —O—, —NH—, —N($C_1$-$C_6$-alkyl)-, —N($C_1$-$C_6$-haloalkyl)-, —S—, —S(O)—, or —S(O)$_2$—, and
wherein 1 to 2 of the carbon atoms of said spirocyclic ring may be optionally and independently substituted with 1 to 2 fluorine, $C_1$-$C_6$-alkyl, $C_1$-$C_6$-haloalkyl, or —$CH_2$O—($C_1$-$C_6$-alkyl);
$R^1$ is selected from the group consisting of H, halogen, and alkyl,
wherein said alkyl is optionally substituted with one or more fluorine, and
wherein 1 to 2 non-adjacent, non-terminal carbon atoms in said alkyl are optionally independently replaced with —O—, —NH—, —N(alkyl)-, —S—, —S(O)—, or —S(O)$_2$—;
$R^2$ and $R^3$ are each independently selected from the group consisting of H, halogen, alkyl, cycloalkyl, -alkyl-cycloalkyl, heterocycloalkyl, -alkyl-heterocycloalkyl, aryl, -alkyl-aryl, heteroaryl, and alkyl-heteroaryl,
wherein each said alkyl, cycloalkyl, heterocycloalkyl, aryl, and heteroaryl of $R^2$ and $R^3$ are optionally substituted with one or more $R^4$, and
wherein 1 to 2 non-adjacent, non-terminal carbon atoms in each said alkyl of $R^2$ and $R^3$ are optionally independently replaced with —O—, —NH—, —N($C_1$-$C_3$-alkyl)-, —S—, —S(O)—, or —S(O)$_2$—,
or, alternatively, $R^2$ and $R^3$ are taken together with the carbon to which they are attached form a spirocyclic ring consisting of from 3 to 6 carbon atoms,
wherein 1 of said carbon atoms may be replaced with —O—, —NH—, —N($C_1$-$C_3$-alkyl)-, —N($C_1$-$C_3$-haloalkyl)-, —S—, —S(O)—, or —S(O)$_2$—, and wherein 1 to 2 of the carbon atoms of said spirocyclic ring may be optionally independently substituted with 1 to 2 fluorine, $C_1$-$C_3$-alkyl, $C_1$-$C_3$-haloalkyl, or —$CH_2$O—($C_1$-$C_3$-alkyl);
ring A is selected from the group consisting of aryl and heteroaryl;
m is 0 or more, with the proviso that the value of m does not exceed the number of available substitutable hydrogen atoms on ring A;
each $R^A$ (when present) is independently selected from the group consisting of halogen, oxo, —OH, —CN, alkyl, —O-alkyl, and cycloalkyl,
wherein said alkyl, —O-alkyl, and cycloalkyl of $R^A$ are each optionally independently unsubstituted or substituted with one or more fluorine, and wherein 1 to 2 non-adjacent, non-terminal carbon atoms in said alkyl and —O-alkyl are optionally independently replaced with —O—, —NH—, —N($C_1$-$C_3$-alkyl)-, —S—, —S(O)—, or —S(O)$_2$—;
n is 1;
-$L_1$ represents a bond or a divalent moiety selected from the group consisting of —O—, —$CH_2$O—, —CH($CH_3$)O—, —CH($CF_3$)O—, and —CH($CHF_2$)O—;
ring B is selected from the group consisting of aryl, heteroaryl, cycloalkyl, and heterocycloalkyl, with the provision that when $L_1$ is —O— or —$CH_2$O—, then ring B is other than cycloalkyl;
p is 0 or more, with the proviso that the value of p does not exceed the number of available substitutable hydrogen atoms on ring B; and
each $R^B$ (when present) is independently selected from the group consisting of halogen, oxo, —OH, —CN, —$SF_5$, —$OSF_5$, —$OR^{B1}$, —$SR^{B1}$, alkyl, alkenyl, alkynyl, cycloalkyl, -alkyl-cycloalkyl, heterocycloalkyl, -alkyl-heterocycloalkyl, aryl, and heteroaryl,
wherein said each alkyl, alkenyl, alkynyl, cycloalkyl, heterocycloalkyl, aryl, and heteroaryl of $R^B$ are each optionally independently unsubstituted or substituted with one or more groups independently selected from $R^4$, and wherein 1 to 2 non-adjacent, non-terminal carbon atoms in said alkyl are optionally independently replaced with —O—, —NH—, —N(alkyl)-, —S—, —S(O)—, or —S(O)$_2$—;
each $R^{B1}$ is independently selected from the group consisting of H, alkyl, alkenyl, alkynyl, cycloalkyl, -alkyl-cycloalkyl, heterocycloalkyl, and alkyl-heterocycloalkyl,
wherein each said alkyl, alkenyl, alkynyl, cycloalkyl, and heterocycloalkyl, of $R^{B1}$ is unsubstituted or optionally substituted with one or more fluorine, and
wherein 1 to 2 non-adjacent, non-terminal carbon atoms in said alkyl are optionally independently replaced with —O—, —NH—, —N($C_1$-$C_6$-alkyl)-, —S—, —S(O)—, or —S(O)$_2$—;
each $R^4$ (when present) is independently selected from the group consisting of halogen, —OH, —CN, $C_1$-$C_6$-alkyl, —($C_1$-$C_6$-alkyl)-OH, —O—($C_1$-$C_6$-alkyl), cycloalkyl, —($C_1$-$C_6$-alkyl)-cycloalkyl, —O-cycloalkyl, —O—($C_1$-$C_6$-alkyl)-cycloalkyl, heterocycloalkyl, —($C_1$-$C_6$-alkyl)-heterocycloalkyl, —O-heterocycloalkyl and —O—($C_1$-$C_6$-alkyl)-heterocycloalkyl,
wherein each said $C_1$-$C_6$-alkyl, cycloalkyl, and heterocycloalkyl are optionally substituted with one or more halogen,
and wherein 1 to 2 non-adjacent, non-terminal carbon atoms in each said $C_1$-$C_6$-alkyl is optionally independently replaced with —O—, —NH—, —N(C$_1$-C$_3$-alkyl)-, —S—, —S(O)—, or —S(O)$_2$—.

2. A compound of claim 1, or a tautomer thereof, or a pharmaceutically acceptable salt of said compound or said tautomer, wherein:
ring C is selected from the group consisting of:

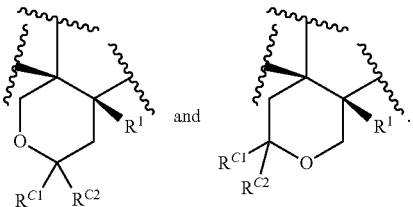

3. A compound of claim 1, or a tautomer thereof, or a pharmaceutically acceptable salt of said compound or said tautomer, wherein:

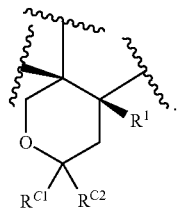

ring C is.

4. A compound of claim 1, or a tautomer thereof, or a pharmaceutically acceptable salt of said compound or said tautomer, wherein:
R$^2$ and R$^3$ are each independently selected from the group consisting of methyl, —CHF$_2$, and —CH$_2$F, cyclopropyl, phenyl, pyridyl, and tetrahydropyranyl,
wherein each said cyclopropyl, phenyl, pyridyl, tetrahydropyranyl of R$^2$ and R$^3$ are unsubstituted or substituted with one or two groups independently selected from the group consisting of fluorine, methyl, ethyl, cyclopropyl, and —OCH$_3$,
wherein each said methyl, ethyl, cyclopropyl, and —OCH$_3$ is each optionally substituted with from 1 to 3 fluoro groups.

5. A compound of claim 1, or a tautomer thereof, or a pharmaceutically acceptable salt of said compound or said tautomer, wherein:
R$^2$ and R$^3$ are methyl.

6. A compound of claim 1, or a tautomer thereof, or a pharmaceutically acceptable salt of said compound or said tautomer, wherein:
n=1;
-L$_1$- is —O—;
ring A is selected from the group consisting of phenyl and pyridinyl;
m is 0, 1, 2, or 3;
each R$^A$ (when present) is fluoro;
ring B is selected from the group consisting of phenyl, piperidinyl, pyrazinyl, pyrazolyl, pyridazinyl, pyridinyl, pyrimidinyl, pyrrolidinyl, tetrahydrofuranyl, tetrahydropyranyl;
p is 0, 1, 2, or 3, with the proviso that the value of p does not exceed the number of available substitutable hydrogen atoms on ring B; and each R$^B$ group (when present) is independently selected from the group consisting of fluoro, chloro, —CN, —OCH$_3$, —O—CH$_2$-cyclopropyl, —O—CH$_2$—C≡, —O—CH$_2$—C≡C—CH$_3$, methyl, ethyl, cyclopropyl, —CH$_2$-cyclopropyl, —CH$_2$OCH$_3$—C≡CH, —C≡C—CH$_3$, —CF$_3$, —CHF$_2$, —OCF$_3$, —OCHF$_2$, oxadiazolyl, isoxazolyl, oxazolyl, pyrazolyl, pyrrolyl, and triazolyl,
wherein each said oxadiazolyl, isoxazolyl, oxazolyl, pyrazolyl, pyrrolyl, and triazolyl, is optionally substituted with one substituent from the group consisting of fluoro and methyl.

7. A compound of claim 1, or a tautomer thereof, or a pharmaceutically acceptable salt of said compound or said tautomer, wherein:
n is 1;
-L$_1$- is —CH$_2$O—;
ring A is selected from the group consisting of phenyl and pyridinyl;
m is 0, 1, 2, or 3;
each R$^A$ (when present) is fluoro;
ring B is selected from the group consisting of oxazolyl, phenyl, pyrazinyl, pyridinyl, pyrimidinyl, tetrahydropyranyl, and thiazolyl;
p is 0, 1, 2, or 3, with the proviso that the value of p does not exceed the number of available substitutable hydrogen atoms on ring B; and
each R$^B$ group (when present) is independently selected from the group consisting of fluoro, chloro, —CN, —OCH$_3$, O—CH$_2$—C≡CH, —O—CH$_2$—C≡C—CH$_3$, methyl, cyclopropyl, —CH$_2$OCH$_3$, —C≡CH, —C≡C—CH$_3$, —CF$_3$, —CHF$_2$, —OCF$_3$, and —OCHF$_2$.

8. A compound of claim 1, or a tautomer thereof, or a pharmaceutically acceptable salt of said compound or said tautomer, wherein:
n=1;
-L$_1$- is a bond;
ring A is selected from the group consisting of phenyl, pyridinyl, and thienyl;
m is 0, 1, 2, or 3;
each R$^A$ (when present) is independently selected from the group consisting of fluoro, chloro, methyl, and —CHF$_2$;
ring B is selected from the group consisting of phenyl, pyridinyl, and pyrimidinyl;
p is 0, 1, or 2; and
each R$^B$ group (when present) is independently selected from the group consisting of fluoro, chloro, methyl, —CN, —OMe, —C≡CH, —C≡C—CH$_3$, and —CHF$_2$.

9. A compound of claim 1, or a tautomer thereof, or a pharmaceutically acceptable salt of said compound or said tautomer, said compound selected from the group consisting of:

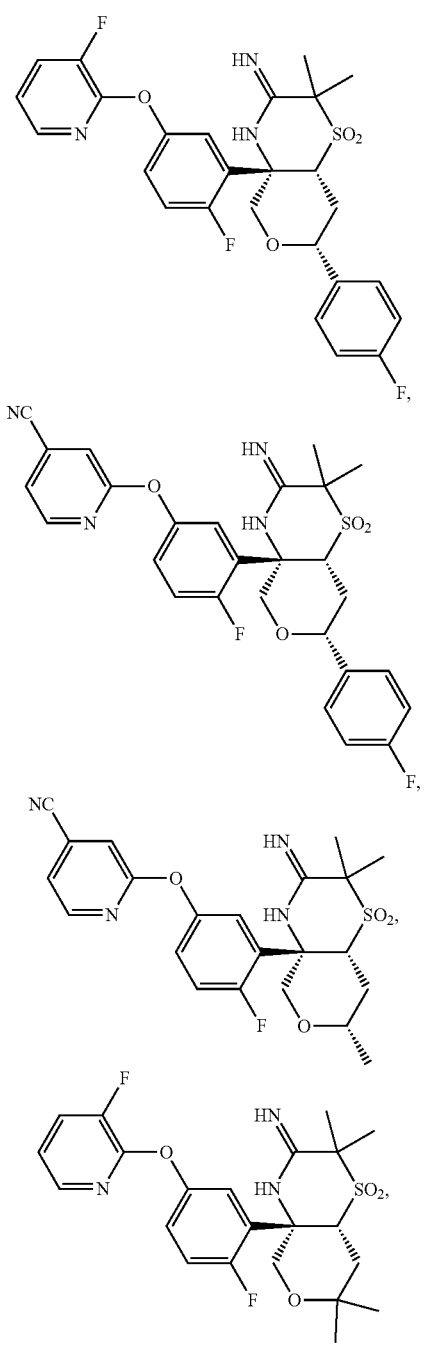
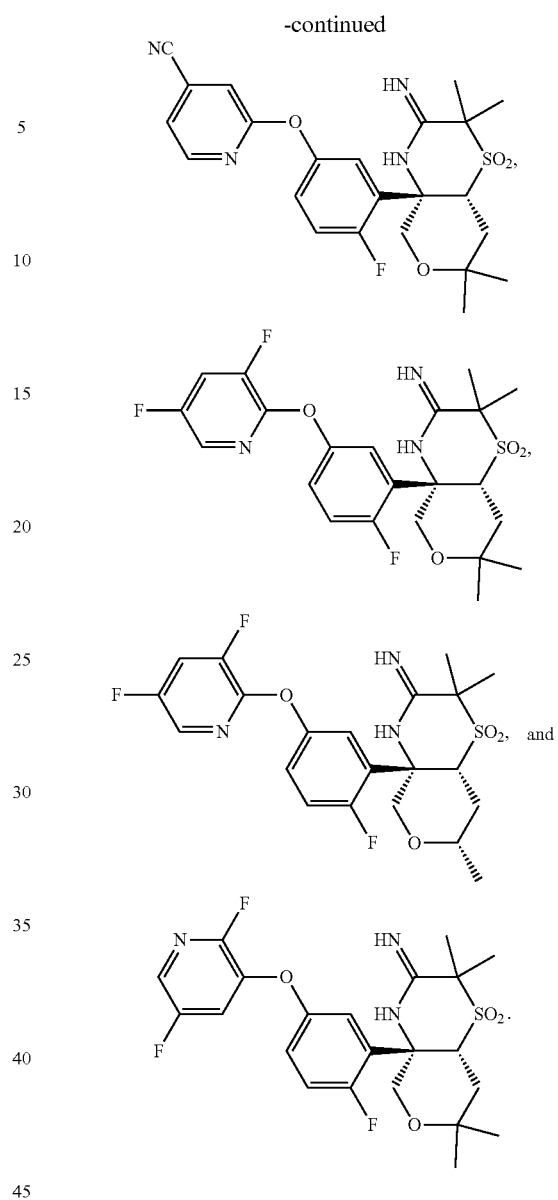
10. A pharmaceutical composition comprising: (i) a compound according to claim 1, or a tautomer thereof, or a pharmaceutically acceptable salt of said compound or said tautomer, and (ii) a pharmaceutically acceptable carrier or diluent.
* * * * *